US008828678B2

(12) United States Patent
Szczepanik et al.

(10) Patent No.: US 8,828,678 B2
(45) Date of Patent: Sep. 9, 2014

(54) SELF-IMMOLATIVE PROBES FOR ENZYME ACTIVITY DETECTION

(75) Inventors: Maciej Szczepanik, Mount Sinai, NY (US); Irina V. Lebedeva, Bronx, NY (US); Yuejun Xiang, Hollis Hills, NY (US); Praveen Pande, Holbrook, NY (US); Wayne Forrest Patton, Dix Hills, NY (US)

(73) Assignee: Enzo Life Sciences, Inc., Farmingdale, NY (US)

( * ) Notice: Subject to any disclaimer, the term of this patent is extended or adjusted under 35 U.S.C. 154(b) by 422 days.

(21) Appl. No.: 12/927,497

(22) Filed: Nov. 16, 2010

(65) Prior Publication Data

US 2012/0122136 A1     May 17, 2012

(51) Int. Cl.
*C12Q 1/26* (2006.01)
*C07D 311/02* (2006.01)
*C07D 305/14* (2006.01)
*C07D 413/00* (2006.01)
*G01N 21/00* (2006.01)

(52) U.S. Cl.
CPC .......... *G09K 11/06* (2013.01); *G01N 2333/902* (2013.01); *C12Q 1/26* (2013.01); *G01N 2500/00* (2013.01)
USPC ............. 435/25; 549/288; 549/265; 544/149; 436/164

(58) Field of Classification Search
CPC .. C07D 311/02; C07D 305/14; C07D 413/00; C12Q 1/26; G01N 21/00
USPC ...................... 435/25; 549/288, 265; 544/149; 436/164
See application file for complete search history.

(56) References Cited

U.S. PATENT DOCUMENTS

| | | | |
|---|---|---|---|
| 6,010,664 A * | 1/2000 | Johnson et al. | 422/62 |
| 7,445,891 B2 | 11/2008 | Taylor | |
| 7,534,902 B2 | 5/2009 | Raines et al. | |
| 7,569,695 B2 | 8/2009 | Xiang et al. | |
| 7,579,140 B2 | 8/2009 | West et al. | |
| 7,662,973 B2 | 2/2010 | Thomas et al. | |
| 7,737,281 B2 | 6/2010 | Szczepanik | |
| 7,754,681 B2 | 7/2010 | Feng | |
| 2002/0031795 A1 | 3/2002 | James et al. | |
| 2003/0186348 A1 | 10/2003 | Thomas et al. | |
| 2005/0032147 A1* | 2/2005 | Jiang et al. | 435/18 |
| 2005/0048317 A1* | 3/2005 | Seo et al. | 428/690 |
| 2005/0271615 A1 | 12/2005 | Shabat et al. | |
| 2006/0024317 A1* | 2/2006 | Boyd et al. | 424/178.1 |
| 2007/0009980 A1 | 1/2007 | Graham | |
| 2009/0253118 A1 | 10/2009 | Yang et al. | |
| 2010/0062460 A1 | 3/2010 | Pande et al. | |
| 2010/0068752 A1 | 3/2010 | Pande et al. | |
| 2010/0081159 A1 | 4/2010 | Lebedeva et al. | |
| 2010/0093004 A1 | 4/2010 | Patton et al. | |
| 2010/0173332 A1 | 7/2010 | Smaill et al. | |
| 2011/0269168 A1 | 11/2011 | Lebedeva et al. | |

FOREIGN PATENT DOCUMENTS

| | | |
|---|---|---|
| WO | WO2005/047245 | 5/2005 |
| WO | WO 2006100417 A1 * | 9/2006 |
| WO | WO2008/030120 | 3/2008 |
| WO | WO2010/017487 | 2/2010 |

OTHER PUBLICATIONS

James et al. J. Heterocytlic Chem. (2006) 43: 515-517.*
Yu et al. Fenxi Shiyanshi (2002) 21(4): 87-89, STN abstract downloaded from CAPLUS Jan. 26, 2013.*
Anastasio, C. and Matthew, B.M., A chemical probe technique for the determination of reactive halogen species in aqueous solution: Part 2—chloride solutions and mixed bromide/chloride solutions, Atmos. Chem. Phys., 2006, 2439-2451, 6.
Chandran et al., Latent Fluorophore Based on the Trimethyl Lock, J. Am. Chem. Soc. 2005, 1652-1653, 127.
Danieli, Eyal and Shabat, Doron, Molecular probe for enzymatic activity with dual output, Bioorganic & Medicinal Chemistry 2007, 7318-7324, 15.
Duimstra et al., A Gadolinium Chelate for Detection of Beta-Glucuronidase: A Self-Immolative Approach, J. Am. Chem. Soc. 2005, 12847-12855, 127.
Gao et al., Novel Fluorogenic Substrates for Imaging Beta-Lactamase Gene Expression, J. Am. Chem. Soc. 2003, 11146-11147, 125.
Ho et al., Development of a dual fluorogenic and chromogenic dipeptidyl peptidase IV substrate, Bioorganic & Medicinal Chemistry Letters 2006, 2599-2602, 16.
Huang et al., Design and Synthesis of a Long-Wavelength Latent Fluorogenic Substrate for Salicylate Hydroxylase: A Useful Fluorimetric Indicator for Analyte Determination by Dehydrogenase-Coupled Biosensors, Anal. Chem. 2010, 7329-7334, 82.
Huang, Sheng-Tung and Lin, Yuh-Ling, New Latent Fluorophore for DT Diaphorase, Organic Letters 2006, 265-268, 8.
Jones et al., An image contrast agent selectively activated by prostate specific antigen, Bioorganic & Medicinal Chemistry 2006, 418-425,14.
Matthew, B.M. and Anastasio, C., A chemical probe technique for the determination of reactive halogen species in aqueous solution: Part 1—bromide solutions, Atmos. Chem. Phys., 2006, 2423-2437, 6.
Meyer et al., Development of a New Nonpeptidic Self-Immolative Spacer. Application to the Design of Protease Sensing Fluorogenic Probes, Organic Letters 2008, 1517-1520, 10.
Nagano, Tetsuo, Bioimaging Probes for Reactive Oxygen Species and Reactive Nitrogen Species, J. Clin. Biochem. Nutr., 2009, 111-124, 45.

(Continued)

*Primary Examiner* — Susan Hanley
(74) *Attorney, Agent, or Firm* — Anna D. DiGabriele Petti, Esq.

(57) ABSTRACT

A compound comprising the structure:

(SIG)-(SI-MOD)$_m$.

is provided in which SIG is a signaling molecule, SI is a self-immolative structure bound to SIG such that SIG has a reduced signal relative to the signal of SIG without SI, MOD is a moiety bound to SI that is subject to modification by an activator, and m is an integer from 1 to about 10. When MOD is modified by an activator, SI is destabilized and self-cleaved from SIG such that SIG generates an increased signal. Also provided are methods of determining whether a sample comprises an activator such as a nitroreductase, and methods of determining whether a mammalian cell is hypoxic using a compound of the formula (SIG)-(SI-MOD)$_m$.

7 Claims, 23 Drawing Sheets

(56) References Cited

OTHER PUBLICATIONS

Nakata et al., Design of a bioreductively-activated fluorescent pH probe for tumor hypoxia imaging, Bioorganic & Medicinal Chemistry 2009, 6952-6958, 17.

Nunn et al., Nitroimidazoles and imaging hypoxia, Eur J Nucl Med 1995, 265-280, 22.

Ojima, Iwao, Guided Molecular Missiles for Tumor-Targeting Chemotherapy—Case Studies Using the Second-Generation Taxoids as Warheads, Accounts of Chemical Research 2008, 108-119, 41.

Pires, Marcos M. and Chmielewski, Jean, Fluorescence Imaging of Cellular Glutathione Using a Latent Rhodamine, Organic Letters 2008, 837-840, 10.

Richard et al., Latent Fluorophores Based on a Self-Immolative Linker Strategy and Suitable for Protease Sensing, Bioconjugate Chem. 2008, 1707-1718, 19.

Richard et al., Chemiluminescent Probe for the in Vitro Detection of Protease Activity, Organic Letters 2007, 4853-4855, 9.

Richard et al., 7-Hydroxycoumarin-Hemicyanine Hybrids: A New Class of Far-Red Emitting Fluorogenic Dyes, Organic Letters 2008, 4175-4178, 10.

Sagi et al., Self-Immolative Polymers, J. Am. Chem. Soc. 2008, 5434-5435, 130.

Tarpey et al., Methods for detection of reactive metabolites of oxygen and nitrogen: in vitro and in vivo considerations, Am J Physiol Regul Integr Comp Physiol 2004, R431-R444, 286.

Ueno et al., Mechanism-Based Molecular Design of Highly Selective Fluorescence Probes for Nitrative Stress, J. Am. Chem. Soc. 2006, 10640-10641, 128.

Varia et al., Pimonidazole: A Novel Hypoxia Marker for Complementary Study of Tumor Hypoxia and Cell Proliferation in Cervical Carcinoma, Gynecologic Oncology 1998, 270-277, 71.

Yatzeck et al., A highly sensitive fluorogenic probe for cytochrome P450 activity in live cells, Bioorganic & Medicinal Chemistry Letters 2008, 5864-5866, 18.

Young, Ian T., Proof without prejudice: use of the Kolmogorov-Smirnov test for the analysis of histograms from flow systems and other sources, J Histochem Cytochem 1977, 935-941, 25.

\* cited by examiner

SELF-IMMOLATIVE PROBES FOR ENZYME ACTIVITY DETECTION

BACKGROUND OF THE INVENTION (1) Field of the Invention

The present invention generally relates to the field of reagents for visual detection, quantification and localization of cells. More specifically, probes are provided that increase their signal upon exposure to specific enzyme or chemical analyte presence.

(2) Description of the Related Art

Signaling molecules that are responsive to the intracellular environment are indispensable tools for fast and accurate detection and measurement of both physiological and pathological processes. However, only a limited number of rationally designed probes or "signalophores" capable of detecting intracellular organic biomolecules exist.

For a chemical molecule to be a suitable signalophore, it should meet several conditions. First, it should have favorable spectral properties, and be detectable by readily available sources and filter systems. Second, it should exhibit a significant signal enhancement triggered by the presence of a specific enzyme activity or analyte to be detected. For the signal-to-background ratio, and as a result the sensitivity of the probe to be maximized, the probe should preferably be "signalogenic"—in a "no-signal" form in the absence of the enzyme or analyte and in "signal on" form in their presence. One of the types of probes fulfilling the above criterion are self-immolative probes.

The concept of self-immolative substrates has been successfully used in designing several prodrugs where the active drug is released upon the activation by a specific chemical trigger. See, e.g., U.S. Pat. Nos. 7,754,681 and 7,445,891. That approach was also used, albeit to much lesser extent, for making markers for probing and detecting specific biological processes and phenomena.

U.S. Pat. No. 7,534,902 describes fluorogenic assays based on the use of a group of self-immolative markers containing a so-called trimethyl lock, which is an aromatic self-immolative group that comprises three methyl groups. Trimethyl locks have been used for detection and measurement of several enzymatic activities including esterases (Chandran et al., 2005; Lavis et al., 2006), DT diaphorase (DTD) (Huang et al., 2006), and cytochrome P450 (Yatzeck et al., 2008).

Self-immolative dendrimers that release multiple fluorescent moieties upon activation have also been developed (US Patent Publication US2005/0271615; Danieli and Shabat, 2007).

Several latent probes have also been designed utilizing a benzyl carbamate self-immolative moiety. A fluorescent image contrast agent selectively activated by prostate specific antigen was described by Jones et al. (2006), while Pires et al. (2008) evaluated cellular glutathione fluorescence imaging using a latent rhodamine derivative.

Substituted benzyl groups as self-immolative substrates were also used by Nakata et al. (2009) for preparing bioreductively-activated fluorescent pH probes for tumor hypoxia imaging. Richard et al. applied that group for preparing a chemiluminescent probe for in vitro detection of protease activity while a long-wavelength latent fluorogenic substrate was utilized as an indicator for dehydrogenase-coupled biosensors (Huang et al., 2010).

Several other self-immolative groups have been used for determination of enzyme activities as well. A traceless linker that is stable under physiological conditions but spontaneously decomposes to a hemithioaminal intermediate upon protease activation is taught by Meyer et al. (2008). Additionally, a Waldmann traceless linker has been utilized for peptidase probes (Richard et al., 2008a). A penicillin G acylase fluorogenic probe is also described by Richard et al., 2008b. Further, a self-immolative disulfide linker carboxylic acid was used to prepare biotin-containing fluorogenic probes for internalization and drug release (Ojima et al., 2008). See also Sagi et al., 2008. Additional self-immolative substrates for detecting enzymes are described in Gao et al. (2003), Duimstra et al. (2005), and Ho et al. (2006).

There is a need for further self-immolative signalogenic markers with a high signal-to-background ratio that are sensitive to specific enzyme or analyte triggers. The present invention addresses that need.

SUMMARY OF THE INVENTION

The present invention provides several self-immolative probes that are useful for detecting enzymes or other activators.

In some embodiments, a compound is provided that comprises the structure:

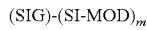

$$(\text{SIG})\text{-}(\text{SI-MOD})_m$$

wherein SIG is a signaling molecule, SI is a self-immolative structure bound to SIG such that SIG has a reduced signal relative to the signal of SIG without SI, MOD is a moiety bound to SI that is subject to modification by an activator, and m is an integer from 1 to about 10. In these embodiments, when MOD is modified by an activator, SI is destabilized and self-cleaved from SIG such that SIG generates an increased signal.

In other embodiments, a method of determining whether a sample comprises an activator is provided. The method comprises (a) incubating the sample with the above-identified compound for a time and under conditions sufficient for MOD to be modified by the activator; and (b) determining whether SIG generates a greater signal than the signal generated by the compound without the activator. In these embodiments, a greater signal indicates that the sample comprises the activator.

Also provided is a method of determining whether a cell comprises a nitroreductase. The method comprises (a) incubating the cell with the above-identified compound, where nitroreductase is the activator, for a time and under conditions sufficient for the compound to enter the cell and be exposed to a nitroreductase if present in the cell; and (b) determining whether SIG generates a greater signal than the signal generated by the compound when not exposed to a nitroreductase. In these embodiments, a greater signal indicates that the cell comprises the nitroreductase.

Additionally provided is a method of determining whether a mammalian cell is hypoxic. The method comprises (a) incubating the cell with the above-identified compound, where nitroreductase is the activator, for a time and under conditions sufficient for the compound to enter the cell and be exposed to a nitroreductase if present in the cell, wherein the nitroreductase is indicative or hypoxia in the cell; and (b) determining whether SIG generates a greater signal than the signal generated by the compound when not exposed to a nitroreductase. In this method, a greater signal indicates that the cell is hypoxic.

A method of detecting a microorganism that comprises a nitroreductase is also provided. The method comprises (a) incubating the microorganism with the above-identified compound, where nitroreductase is the activator, for a time and under conditions sufficient for the compound to enter the cell and be exposed to a nitroreductase if present in the microorganism; and (b) determining whether SIG generates a greater signal than the signal generated by the compound when not exposed to a nitroreductase. In this method, a greater signal indicates that the microorganism comprises a nitroreductase.

In additional embodiments, a method of identifying nitroreductase in a sample is provided. The method comprises (a) incubating the sample with the with the above-identified compound, where nitroreductase is the activator, then (b) determining whether SIG generates a greater signal than the signal generated by the compound when not exposed to a nitroreductase. Here, a greater signal indicates that the sample comprises a nitroreductase.

BRIEF DESCRIPTION OF THE FIGURES

FIG. 6A shows double staining with the hypoxia CD-5 probe and the ROS probe DCFDA (top mei), single staining with the hypoxia CD-5 probe (middle panel) and single staining with the ROS probe DCFDA (bottom panel), FIG. 6B shows double staining with the hypoxia CD-5 probe and the ROS probe HE (top panel), single staining with the hypoxia CD-5 probe (middle panel), and single staining with the ROS probe HE (bottom panel). FIG. 6C shows double staining with the hypoxia CD-1 probe and the ROS probe HE (top panel), single staining with the hypoxia CD-1 probe middle panel single staining with the ROS probe HE (bottom panel).

FIG. 7A shows the detection of an increased population of green positive cells when the CD-1 hypoxia probe is used in combination with superoxide detection. FIG. 7B shows that cells stained oral with the CD-1 hypoxia probe exhibits similar numbers for green positive populations. FIG. 7C shows that the hypoxia probe CD-6 was able to detect hypoxic cell populations when used in combination with ROS probes.

FIG. 8A shows that hypoxia probe CD-6 was able to detect hypoxic cell populations when used with a superoxide detection reagent. FIG. 8B shows that hypoxia probe CD-6 was able to detect hypoxic cell populations when used with an oxidative stress detection reagent. FIG. 8C shows that the CD-6 hypoxia probe was able to detect hypoxic cell populations when used alone. FIG. 8D shows corroboration of data by staining of pyocyanin-treated cells (a positive control for ROS production) and by analyzing samples stained with ROS-detecting reagents.

DETAILED DESCRIPTION OF THE INVENTION

As used herein, the singular forms "a", "an" and "the" are intended to include the plural forms as well, unless the context clearly indicates otherwise. Additionally, the use of "or" is intended to include "and/or", unless the context clearly indicates otherwise.

As used herein, a "self-immolative probe" refers to a signaling molecule covalently bound to a moiety (a "self-immolative arm") such that the self-immolative arm inhibits the signaling molecule from signaling. The self immolative arm is covalently bound to an enzyme substrate such that the action of the enzyme causes a destabilization of the self-immolative arm such that the self immolative arm becomes removed from the signaling molecule, allowing the signaling molecule to signal.

As used herein, "hypoxic" cells are cells with inadequate oxygen. Such cells are also "anoxic," which refers to a complete deprivation of oxygen.

Figure 1:
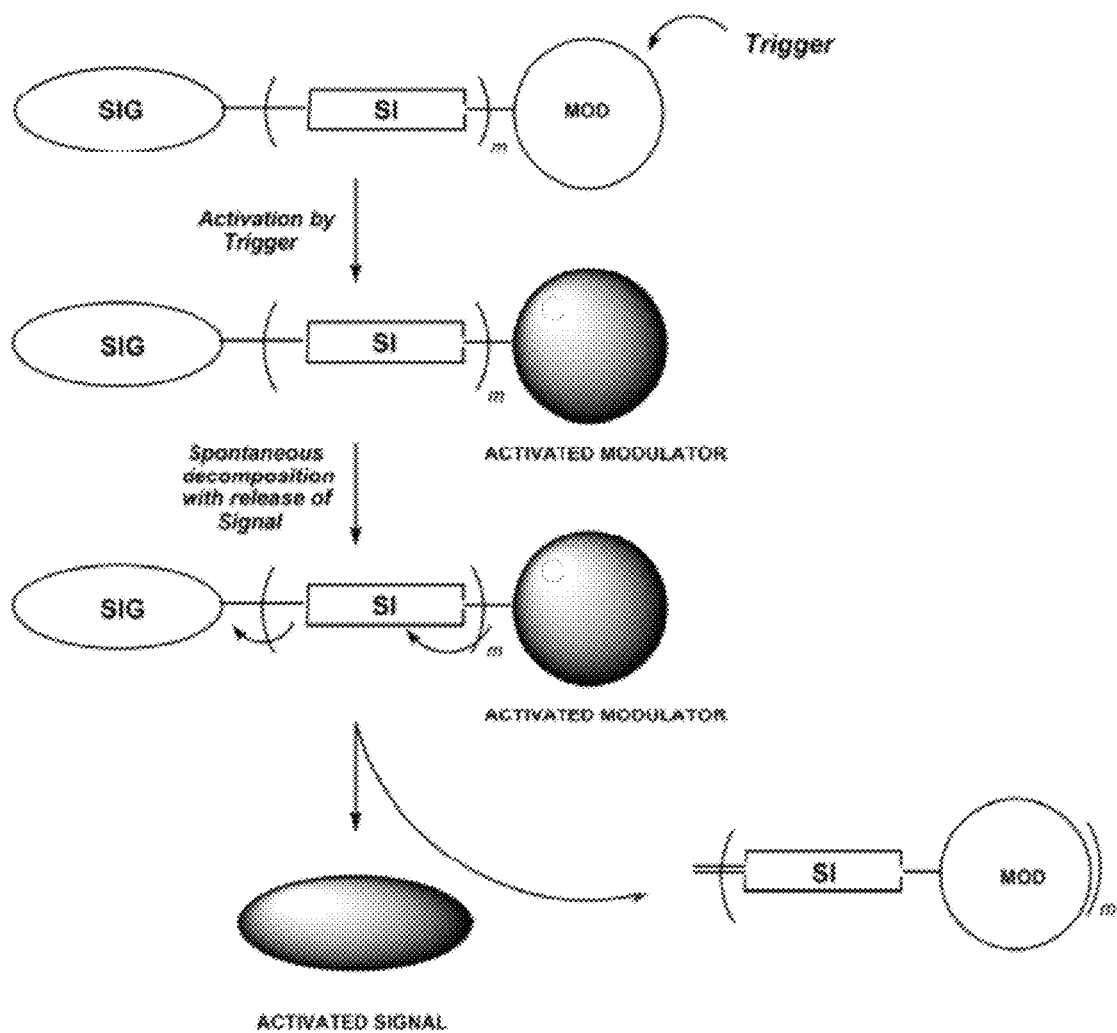
FIG. 1 is an illustration of the mechanism of action of self-immolative probes of the present invention.

The present invention provides probes that may be used in the detection of specific enzyme activities or the presence of an analyte in vivo or in vitro. Structurally the probes represent signalogenic molecules comprising a signaling molecule, SIG, functionalized with one or more self-immolative groups, SI, and a modulator, MOD. The mechanism of action of these probes is illustrated in FIG. 1. The self-immolative group(s), SI, attached to the signal, SIG, produce a signalogenic, usually colorless, non-fluorescent or non-luminescent, compound. The signal SIG, defined as the colored, fluorescent or luminescent dye, is released from the probe by a specific chemical activator ("Trigger" in FIG. 1) that acts on MOD and causes cleavage of SI from SIG. The activator is, for example, an enzyme or an analyte that the probe serves to detect. The released signal molecule SIG can be detected by any means appropriate for the specific SIG, such as UV-Vis spectroscopy, fluorescence microscopy, flow cytometry, fluorescence spectroscopy or any other method known in the art. The intensity of the signal generated may be quantified.

The signalogenic compounds of the present invention can be represented by the following general formula:

(SIG)-(SI-MOD)$_m$ wherein SIG is a signaling molecule, SI is a self-immolative structure bound to SIG such that SIG has a reduced signal relative to the signal of SIG without SI, MOD is a moiety bound to SI that is subject to enzymatic modification, and m is an integer from 1 to about 10. When MOD is modified by an activator, SI is destabilized and self-cleaved from SIG such that SIG generates an increased signal. SIG in the above structure can be any signaling molecule including, but not limited to, a fluorophore, a chromophore, a luminescent compound etc.

In some embodiments, the compound comprises

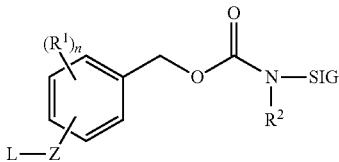

wherein

L-Z is MOD and is ortho or para to the benzyl carbamate group, wherein

Z is a reducible nitrogen-containing group, or an amino group with an electron-deficient moiety, and L is nothing when Z is a reducible nitrogen-containing group, otherwise L is an unsubstituted straight-chain, branched or cyclic alkyl, alkenyl or alkynyl group, a substituted straight-chain, branched or cyclic alkyl, alkenyl or alkynyl group wherein one or more C, CH or CH$_2$ groups are substituted with an O atom, N atom, S atom, or NH group, an unsubstituted or substituted aromatic group, or a linear or branched sequence of amino acids;

each R$^1$ is independently a hydrogen, a halogen, a Z, a cyano group (CN), an isocyano group (NC), a thiocyano group (SCN), an isothiocyano group (SNC), an azido group (N$_3$), a trihalomethyl group (CX$_3$, where X is a halogen); a sulfonate group (SO$_3$R$^3$), a sulfate group (OSO$_3$R$^3$), a carboxyl group (CO$_2$H), a carbonyl group (COR$^S$), an ester group (CO$_2$R$^3$ or OCOR$^3$), an amido group (CONR$^3$$_2$ or NR$^3$COR$^3$), a carbamate group (NR$^3$CO$_2$R$^3$), a phosphate group (OPO$_3$R$^3$$_3$), a phosphonate group (PO$_3$R$^3$$_2$), an amino group (NR$^3$$_2$), an alkoxy group (OR$^S$), a thiol group (SR$^S$), a sulfoxy group (SOR$^3$), a sulfone group (SO$_2$R$^3$), a sulfonamide group (SO$_2$NR$^3$$_2$), a phosphino group (PR$^3$$_2$), or a silane group (SiR$^3$$_3$);

each R$^3$ is independently a hydrogen, an unsubstituted straight-chain, branched or cyclic alkyl, alkenyl or alkynyl group, a substituted straight-chain, branched or cyclic alkyl, alkenyl or alkynyl group wherein one or more C, CH or CH$_2$ groups are substituted with an O atom, N atom, S atom, or NH group, or an unsubstituted or substituted aromatic group;

n is 0, 1, 2, 3 or 4; and

R$^2$ is a hydrogen, an unsubstituted straight-chain, branched or cyclic alkyl, alkenyl or alkynyl group, a substituted straight-chain, branched or cyclic alkyl, alkenyl or alkynyl group wherein one or more C, CH or CH$_2$ groups are substituted with an O atom, N atom, S atom, NH group, CO group, OCO group or CONR$^3$ group, or an unsubstituted or substituted aromatic group.

In some of these embodiments, Z is a reducible nitrogen-containing group selected from the group consisting of a nitro group (NO$_2$), an azo group (N=N), a hydrazo group (NH—NH), a nitroso group (NO), and a hydroxylamino group (NHOH). These embodiments are particularly useful where the activator is a nitroreductase. See Examples.

In other embodiments, Z is an amino group with an electron-deficient moiety, for example a carbonyl (C=O), a phosphoryl (PO$_3$$^{2-}$) or a sulfonyl (SO$_3$$^-$) moiety.

In additional embodiments, Z is an amino group with an electron-deficient moiety and L is an amino acid sequence that is a substrate for an activator that is an enzyme. In these embodiments, the enzyme is capable of cleaving L from Z, leading to self-cleavage of SI and releasing SIG-NR$^2$.

The mechanism of action of these self-immolative probes can be illustrated for the specific embodiments where Z is NO$_2$, the activator is a nitroreductase, and SIG is a fluorophore, as follows. When exposed to nitroreductase, the nitrobenzyl carbamate group undergoes the following reaction:

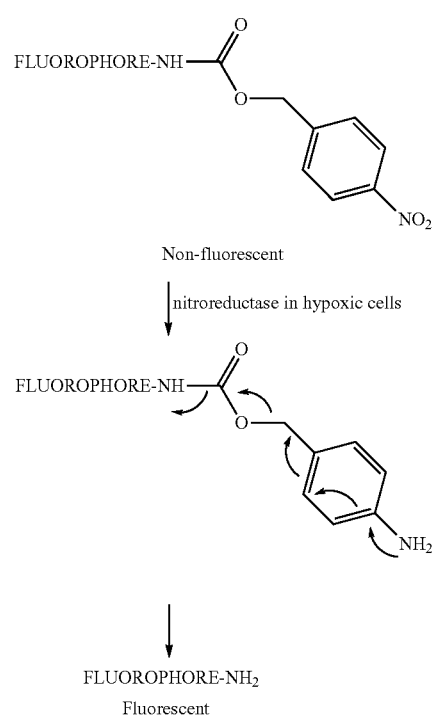

In this scheme, the fluorophore probe comprising the nitrobenzyl carbamate moiety will not fluoresce due to the electron withdrawing character of that moiety. The nitroreductase reduces the nitro group to an amino group, which contributes an electron to the benzyl group, causing a domino-like electron transfer through the structure, resulting in destabilization and cleavage of the nitrobenzyl carbamate moiety at the carbamate amino group. The electron-withdrawing nature of the nitrobenzyl carbamate moiety, which resulted in a lack of fluorescence of the fluorophore, is thus removed, allowing the fluorophore to fluoresce.

Another example of the self-immolative probes of the present invention comprises

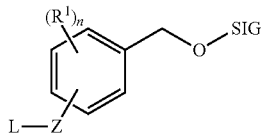

wherein

L-Z is MOD and is ortho or para to the benzyl group, wherein

Z is a reducible nitrogen-containing group, or an amino group with an electron-deficient moiety, and L is nothing when Z is a reducible nitrogen-containing group, otherwise L is an unsubstituted straight-chain, branched or cyclic alkyl, alkenyl or alkynyl group, a substituted straight-chain, branched or cyclic alkyl, alkenyl or alkynyl group wherein one or more C, CH or $CH_2$ groups are substituted with an O atom, N atom, S atom, or NH group, an unsubstituted or substituted aromatic group, or a linear or branched sequence of amino acids;

each $R^1$ is independently a hydrogen, a halogen, a Z, a cyano group (CN), an isocyano group (NC), a thiocyano group (SCN), an isothiocyano group (SNC), an azido group ($N_3$), a trihalomethyl group ($CX_3$, where X is a halogen); a sulfonate group ($SO_3R^3$), a sulfate group ($OSO_3R^3$), a carboxyl group ($CO_2H$), a carbonyl group ($COR^5$), an ester group ($CO_2R^3$ or $OCOR^3$), an amido group ($CONR^3_2$ or $NR^3COR^3$), a carbamate group ($NR^3CO_2R^3$), a phosphate group ($OPO_3R^3_3$), a phosphonate group ($PO_3R^3_2$), an amino group ($NR^3_2$), an alkoxy group ($OR^3$), a thiol group ($SR^3$), a sulfoxy group ($SOR^3$), a sulfone group ($SO_2R^3$), a sulfonamide group ($SO_2NR^3_2$), a phosphino group ($PR^3_2$), or a silane group ($SiR^3_3$);

each $R^3$ is independently a hydrogen, an unsubstituted straight-chain, branched or cyclic alkyl, alkenyl or alkynyl group, a substituted straight-chain, branched or cyclic alkyl, alkenyl or alkynyl group wherein one or more C, CH or $CH_2$ groups are substituted with an O atom, N atom, S atom, or NH group, or an unsubstituted or substituted aromatic group; and n is 0, 1, 2, 3 or 4.

As with the previously described probes, in some embodiments of these probes, Z is a reducible nitrogen-containing group selected from the group consisting of a nitro group ($NO_2$), an azo group (N=N), a hydrazo group (NH—NH), a nitroso group (NO), and a hydroxylamino group (NHOH). Such probes are useful for detecting a nitroreductase, which would serve as an activator of the probe. In other embodiments, Z is an amino group with an electron-deficient moiety selected from the group consisting of carbonyl (C=O), phosphoryl ($PO_3^{2-}$) and sulfonyl ($SO_3^-$). In additional embodiments, Z is an amino group with an electron-deficient moiety and L is an amino acid sequence that is a substrate for an activator that is an enzyme, wherein the enzyme is capable of cleaving L from Z, leading to self-cleavage of SI and releasing $SIG-NR^2$.

Still another example of a self-immolative probe of the present invention is a compound comprising the structure

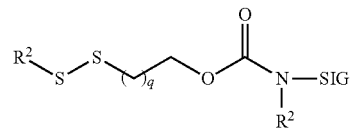

wherein

S—S is MOD;

each $R^2$ is independently a hydrogen, an unsubstituted straight-chain, branched or cyclic alkyl, alkenyl or alkynyl group, a substituted straight-chain, branched or cyclic alkyl, alkenyl or alkynyl group wherein one or more C, CH or $CH_2$ groups are substituted with an O atom, N atom, S atom, NH group, CO group, OCO group or $CONR^3$ group, or an unsubstituted or substituted aromatic group; and q is an integer from 1 to 4.

These probes are particularly useful for detecting disulfide reducing agents, which reduce the disulfide bond, inducing cyclization with a release of a thiolactone and resulting in destabilization and cleavage of the self-immolative moiety to leave the active signaling molecule $SIG-NR^2$. Nonlimiting examples of disulfide reducing agents are glutathione, cysteine, and homocysteine. Thus, this probe can detect any of those compounds.

In some embodiments of the generalized probe

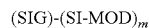

(SIG)-(SI-MOD)$_m$ m>1; in other embodiments, m=1. In some applications, m is preferably 1, so that only one self-immolative group needs to be removed to achieve full signal intensity of the signalophore, SIG. When one self-immolative group is desired but the fluorophore has more than one moiety where the self-immolative group can be attached, a blocker group that preferably does not substantially interfere with the signal, SIG, can be bonded to any reactive moiety on SIG where the self-immolative group is not desired.

Thus, in some embodiments, SIG further comprises at least one blocker moiety that blocks sites of potential SI-MOD attachment during synthesis of the compound, wherein the moiety does not substantially interfere with the SIG signal.

An example of a useful blocker moiety is the urea moiety $R^4_2N—CO—NR^4$, where the compound is

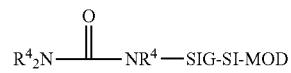

wherein each $R^4$ is independently a hydrogen, an unsubstituted straight-chain, branched or cyclic alkyl, alkenyl or alkynyl group, a substituted straight-chain, branched or cyclic alkyl, alkenyl or alkynyl group wherein one or more C, CH or $CH_2$ in any of the foregoing groups can be substituted with an O atom, N atom, S atom, NH group, CO group, OCO group or $CONR^3$ group, an unsubstituted aromatic group or a substituted aromatic group. In some of these embodiments, two or more $R^4$ groups are fused to form a ring, the ring comprising one or more heteroatoms, wherein the heteroatoms are the same heteroatoms or different heteroatoms. An example of such a blocker moiety is

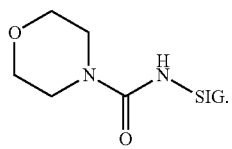

See, e.g., Example 1.

The signalogenic probes of the formula (SIG)-(SI-MOD)$_m$ in this invention can be prepared by any means known in the art, for example by reacting the signal molecule, SIG, with self-immolative group(s), SI, as well as optionally with blocker groups. In some embodiments, the signal molecule reacts with one or more optional blocker groups and then undergoes the reaction with one or more self-immolative groups to give a molecule (SIG)-(SI-MOD)$_m$. The molecule (SIG)-(SI-MOD)$_m$ has a substantially lower signal intensity (fluorescence, luminescence or color intensity) than SIG optionally substituted with the blocker. However, the reactions leading to attachment of self-immolative groups as well as blocker groups to SIG can be performed in any order. This order is conveniently determined by the reaction type and nature of the signal molecule, and can be determined by the skilled artisan without undue experimentation.

The signal, SIG, can be any chemical compound that has decreased fluorescence, luminescence or color intensity when functionalized with one or more self-immolative groups, SI, and increased fluorescence, luminescence or color intensity when at least one of these self-immolative group is removed. Preferably, SIG should be non-fluorescent, non-luminescent and colorless when SI is attached and intensely fluorescent, luminescent or colored when SI is removed. Additionally, SIG should contain or should be readily modified to contain reactive functionalities, as further discussed below, to which both self-immolative and optional blocker moieties could be attached to form a probe.

The invention is not narrowly limited to the use of any particular SIG. In various embodiments, SIG is a chromophore, a fluorophore, a luminescent moiety, an enzyme, a catalytic antibody, a ribozyme or a pro-enzyme.

In some embodiments, SIG is a fluorophore. Any fluorophore now known or later discovered can be utilized in these compounds. Examples of useful fluorophores include without limitation a symmetric or asymmetric cyanine dye, a merocyanine dye, a styryl dye, an oxazine dye, a xanthene dye, a coumarin dye or an iminocoumarin dye.

One class of the signal molecule, SIG, useful in the invention has a xanthene backbone shown in Scheme I below. The structures include both classical xanthene dyes and their lactone forms (Structures A and B, respectively) as well as aphenylic counterparts, which have their appended phenyl ring missing (Structures C).

Scheme I

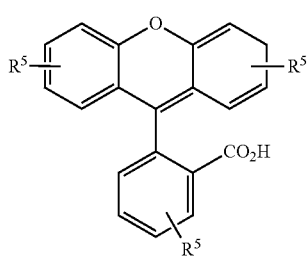

(A)

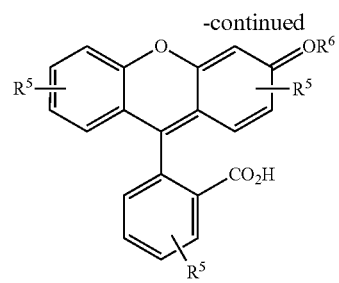

(B)

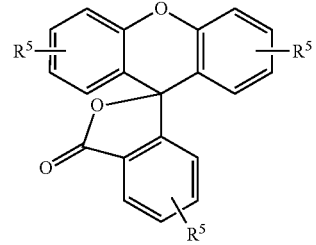

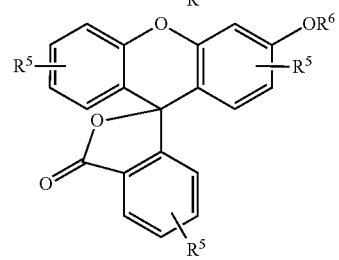

(C)

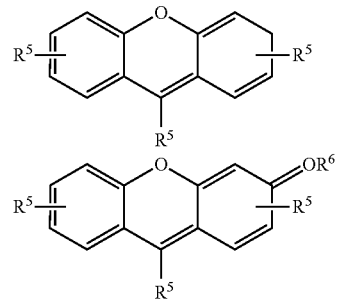

The substituent $R^5$ in Scheme I represents a variety of functionalities where at least one $R^5$ is a reactive group, which allows the attachment of the self-immolative group SI and, if desired, at least one other $R^5$ is a reactive group, which allows the attachment of a blocker moiety. The $R^5$s may be structurally the same or different and there may be several of them per ring. Also, some of the rings may not have any $R^5$s attached. Suitable examples of $R^5$ include, but are not limited to hydrogen, a halogen (F, Cl, Br, I), a nitro group (NO$_2$), a nitroso group (NO), a hydroxylamino group (NHOH), a cyano group (CN), an isocyano group (NC), a thiocyano group (SCN), an isothiocyano group (SNC), an azido group (N$_3$), a trihalomethyl group (CX$_3$, where X is a halogen), a sulfonate group (SO$_3$R$^6$), a sulfate group (OSO$_3$R$^6$), a carboxyl group (CO$_2$H), a carbonyl group (COR$^6$), an ester group (CO$_2$R$^6$ or OCOR$^6$), an amide group (CONR$^6_2$ or NR$^6$COR$^6$), a carbamate group (NR$^6$CO$_2$R$^6$ or OCONR$^6_2$), a phosphate group (OPO$_3$R$^6_3$), a phosphonate group (PO$_3$R$^6_2$), an amino group (NR$^6_2$), an alkoxy group (OR$^6$), a thiol group (SR$^6$), a sulfoxy group (SOR$^6$), a sulfone group (SO$_2$R$^6$), a sulfonamide group (SO$_2$NR$^6_2$), a phosphino group (PR$^6_2$), a silane group (SiR$^6_3$), an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^6$ group, or an optionally substituted aromatic group. In these embodiments, each $R^6$ is independently hydrogen, an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^6$ group, or an optionally substituted aromatic group.

Two or more $R^5$ groups in these fluorophores can be linked together to form rings containing one or more of the same or different heteroatoms, such as O, N or S.

Substituents $R^5$ in these fluorophores that are not directly involved in attachment of self-immolative or urea-containing groups may be present in the molecule for other reasons. These reasons may include modification of spectroscopic characteristics of the dye, its solubility, chemical stability or photobleaching resistance. Some substituents $R^5$ may be useful for binding to a biomolecule or structure to be studied, such as nucleic acid, protein or lipid.

As discussed above, one of the $R^5$ or $R^6$ groups is, or can be substituted to contain, a reactive group thereby allowing the dyes of the present invention to be attached to an SI-MOD group. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use in these embodiments. Examples include but not be limited to isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group.

One class of xanthene fluorophores useful in the present invention includes but not limited to rhodamine and rhodamine derivatives, such as Pennsylvania Green, Tokyo Green, Oregon Green, Singapore Green, and rosamines and rhodols and their derivatives. Some of these derivatives are shown below in Scheme II. The rhodamine, rosamine and rhodol backbone structures can be extended by adding additional rings as shown in Scheme III, or their appended phenyl ring might be missing to form aphenylic counterparts.

Scheme II

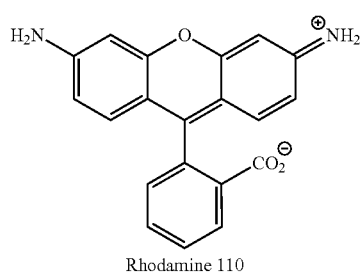

Rhodamine 110

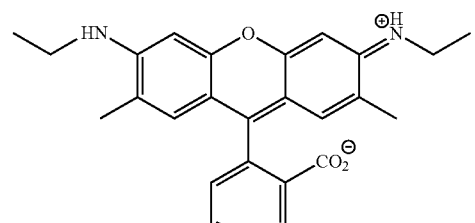

Rhodamine 575

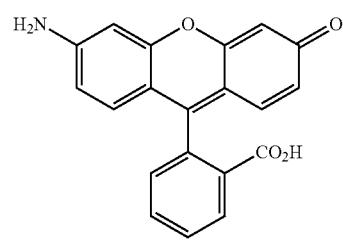

Rhodol

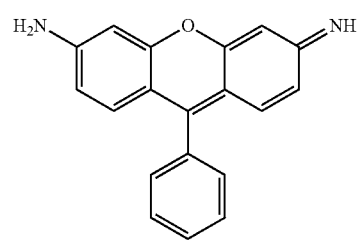

Rosamine

Scheme III

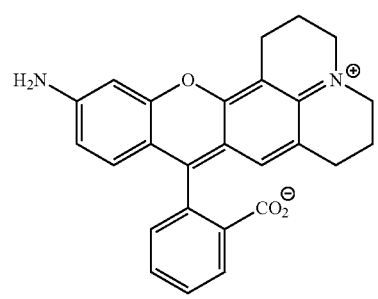

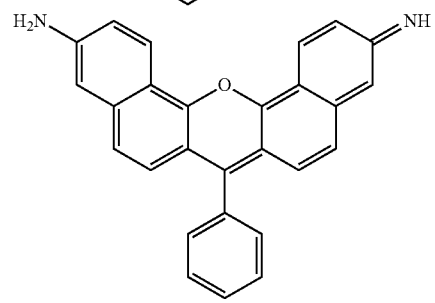

Another class of fluorescent dyes pertinent to the present invention is derivatized from the aforementioned rhodamines, rosamines and rhodols and can be represented by the general structures shown in Scheme IV.

Scheme IV

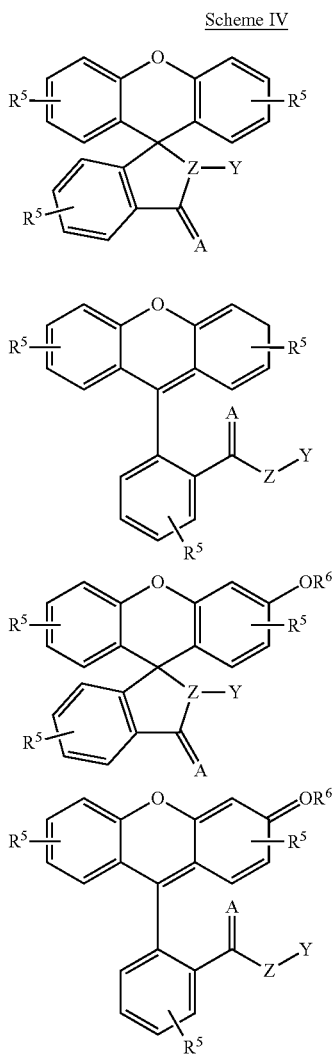

The substituent $R^5$ in Scheme IV is defined as described for Scheme I. The moiety A can be oxygen or sulfur while Z can be oxygen, sulfur or nitrogen unsubstituted or substituted with a group Y. The group Y, in turn, can be hydrogen, an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^3$ group, or an optionally substituted aromatic group. Y can also be another nitrogen, oxygen or sulfur atom substituted with hydrogen or an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^3$ group, or an optionally substituted aromatic group. The substituent, Y, can be a part of an aliphatic or aromatic cyclic structure such as morpholine, piperidine, pyrrolidine, piperazine, imidazole, triazole, oxazole, thiazole and others known in the art. Additionally, both Z and Y can contain electrophilic or nucleophilic reactive groups defined above.

Yet another class of fluorescent dyes pertinent to the present invention is based on coumarin and iminocoumarin backbone structure shown in Scheme V.

Scheme V

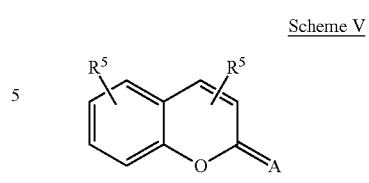

The substituent $R^5$ in the Scheme V represents functionalities defined in Scheme I above while A can be oxygen atom, O, or imino group, NH. Some of the compounds in this category are shown below in Scheme VI. The backbone structure can be extended by adding additional rings, aliphatic or aromatic, substituted or unsubstituted.

Scheme VI

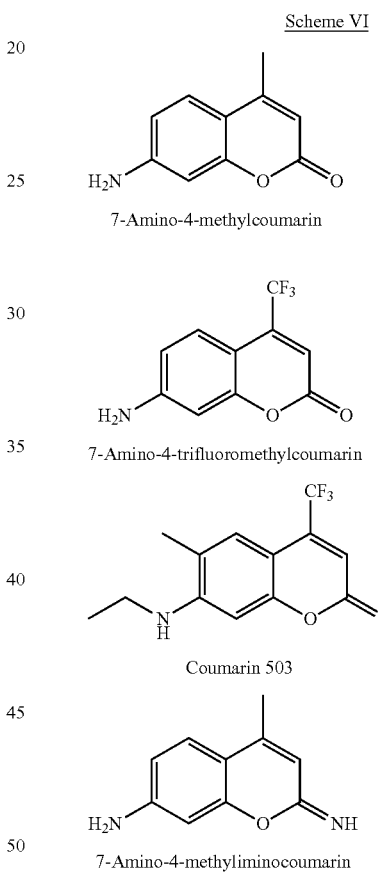

7-Amino-4-methylcoumarin

7-Amino-4-trifluoromethylcoumarin

Coumarin 503

7-Amino-4-methyliminocoumarin

In other embodiments of the compounds of the present invention, SIG is a luminescent moiety. Any luminescent moiety, including any chemiluminescent or bioluminescent moieties, now known or later discovered, can be utilized in these embodiments. In some aspects of these embodiments, the compound comprises the structure:

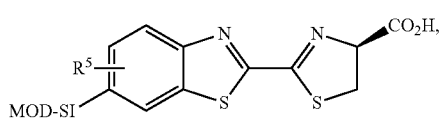

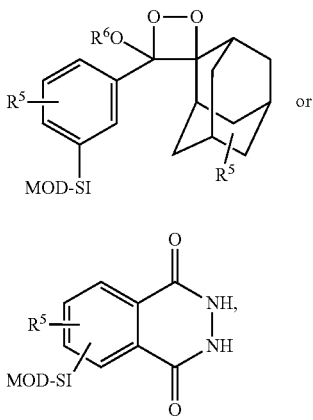

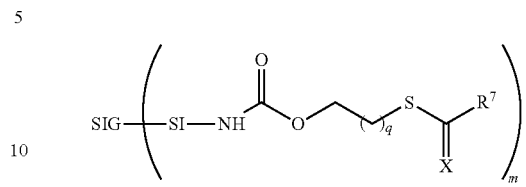

wherein q is an integer from 1 to 4,

X is an oxygen or sulfur, and $R^7$ is an unsubstituted straight-chain, branched or cyclic alkyl, alkenyl or alkynyl group, a substituted straight-chain, branched or cyclic alkyl, alkenyl or alkynyl group wherein one or more C, CH or $CH_2$ in any of the foregoing groups can be substituted with an O atom, N atom, S atom, NH group, CO group, OCO group or $CONR^3$ group, an unsubstituted aromatic group or a substituted aromatic group.

In more particular embodiments, the compound comprises the structure:

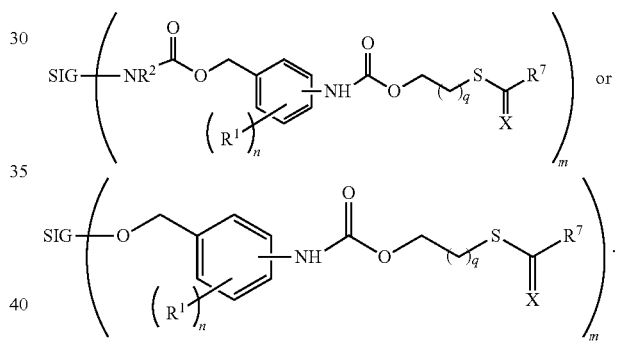

These compounds are useful for esterase or lipase detection, where the enzyme cleaves the thioester bond, causing spontaneous self-immolative collapse of the SI moiety and concomitant release of SIG.

In other embodiments, the enzyme is a nitroreductase. Exemplary compounds that are useful for nitroreductase activation comprise the structures

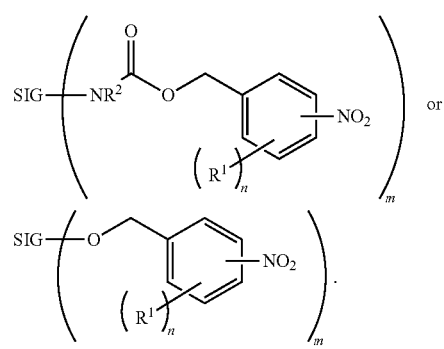

wherein each $R^5$ is independently hydrogen, a halogen (F, Cl, Br, I), a nitro group ($NO_2$), a nitroso group (NO), a hydroxylamino group (NHOH), a cyano group (CN), an isocyano group (NC), a thiocyano group (SCN), an isothiocyano group (SNC), an azido group ($N_3$), a trihalomethyl group ($CX_3$, where X is a halogen); a sulfonate group ($SO_3R^6$), a sulfate group ($OSO_3R^6$), a carboxyl group ($CO_2H$), a carbonyl group ($COR^6$), an ester group ($CO_2R^6$ or $OCOR^6$), an amide group ($CONR^6_2$ or $NR^6COR^6$), a carbamate group ($NR^6CO_2R^6$ or $OCONR^6_2$), a phosphate group ($OPO_3R^6_3$), a phosphonate group ($PO_3R^6_2$), an amino group ($NR^6_2$), an alkoxy group ($OR^6$), a thiol group ($SR^6$), a sulfoxy group ($SOR^6$), a sulfone group ($SO_2R^6$), a sulfonamide group ($SO_2NR^6_2$), a phosphino group ($PR^6_2$), a silane group ($SiR^6_3$), an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^6$ group, or an optionally substituted aromatic group; and each $R^6$ is independently hydrogen, an optionally substituted straight-chain, branched or cyclic alkyl, alkenyl or alkynyl group wherein one or more C, CH or $CH_2$ groups can be replaced with O atom, N atom, S atom, NH group, CO group, OCO group, $CONR^6$ group, or an optionally substituted aromatic group.

The activator for the compounds of the present invention can be any chemical that can modify MOD such that SI is destabilized and self-cleaved from SIG. For example, as discussed above, the activator for some SI-MOD embodiments can be a disulfide reducing agent such as glutathione, cysteine, or homocysteine. In other embodiments, the activator is an enzyme.

Where the activator is an enzyme, the invention is not limited to any particular enzyme, as it is believed that a MOD can be designed for any enzyme without undue experimentation. Nonlimiting examples of enzyme-activators that can be utilized for these embodiments include nitroreductases, kinases, aminopeptidases, esterases, lipases, proteases, peptidases, phosphatases, sulfatases, sulfotransferases, carboxylases, decarboxylases, glycosylases, amidases, deamidases, aminases, deaminases, acetyltransferases, methylases, deacetylases, demethylases, and acetylases.

Specific examples of such compounds include
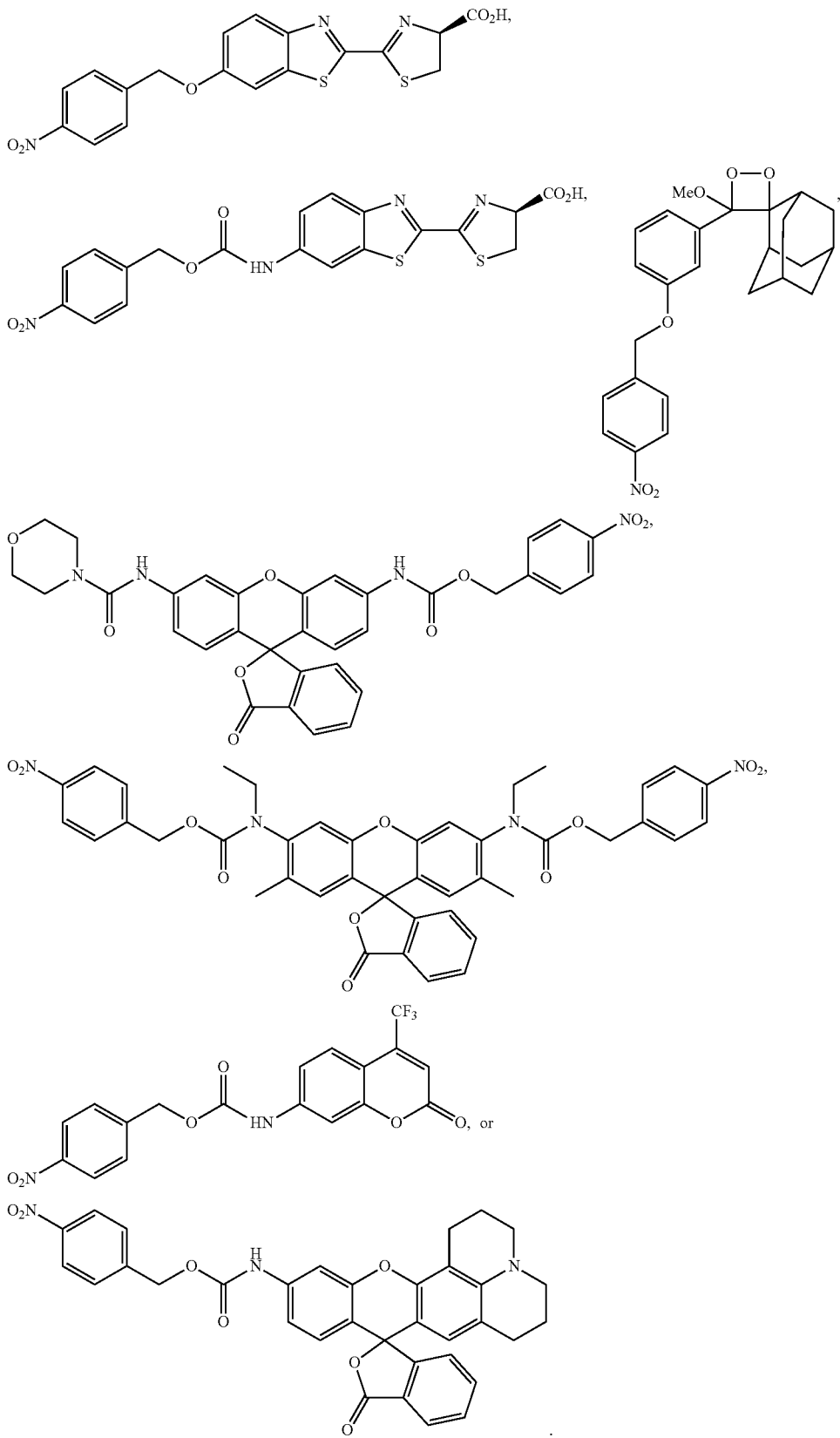

In these embodiments, when the probe is activated by nitroreductase or the enzymes that have nitroreductase activity, the nitro group(s) gets reduced to amino- and hydroxylamino functionalities. This conversion triggers a self-immolative decomposition of the probe with a release of SIG.

Nitroreductases include a broad family of enzymes that reduce nitrogen-containing compounds including those containing the nitro functional group. Members of this family utilize FMN as a cofactor and are often found to be homodimers. Nitroreductases include enzymes from: EC 1.1: which includes oxidoreductases that act on the CH—OH group of donors, EC 1.2: which includes oxidoreductases that act on the aldehyde or oxo group of donors, EC 1.3: which includes oxidoreductases that act on the CH—CH group of donors, EC 1.4: which includes oxidoreductases that act on the CH—NH$_2$ group of donors, EC 1.5: which includes oxidoreductases that act on CH—NH group of donors, EC 1.6: which includes oxidoreductases that act on NADH or NADPH, EC 1.7: which includes oxidoreductases that act on other nitrogenous compounds as donors, EC 1.8: which includes oxidoreductases that act on a sulfur group of donors, EC 1.9: which includes oxidoreductases that act on a heme group of donors, EC 1.10: which includes oxidoreductases that act on diphenols and related substances as donors, EC 1.11: which includes oxidoreductases that act on peroxide as an acceptor (peroxidases), EC 1.12: which includes oxidoreductases that act on hydrogen as donors, EC 1.13: which includes oxidoreductases that act on single donors with incorporation of molecular oxygen (oxygenases), EC 1.14: which includes oxidoreductases that act on paired donors with incorporation of molecular oxygen, EC 1.15: which includes oxidoreductases that act on superoxide radicals as acceptors, EC 1.16: which includes oxidoreductases that oxidize metal ions, EC 1.17: which includes oxidoreductases that act on CH or CH2 groups, EC 1.18: which includes oxidoreductases that act on iron-sulfur proteins as donors, EC 1.19: which includes oxidoreductases that act on reduced flavodoxin as a donor, EC 1.21: which includes oxidoreductases that act on X—H and Y—H to form an X—Y bond, and EC 1.97: which includes other oxidoreductases. Specific examples of nitroreductases include DT-diaphorase [NQ01; E.C.1.6.99.2]; cytochrome P450-reductase [CYPOR; E.C.1.6.2.4]; inducible nitric oxide synthase [NOS2A; E.C.1.14.13.39]; cytochrome B5 reductase [DIAL; E.C.1.6.2.2]; xanthine oxidase [XO; E.C.1.17.3.2]; xanthine dehydrogenase [XDH; E.C.1.17.1.4]; adrenodoxin oxidoreductase [FDXR; E.C.1.18.1.2]; methionine synthase reductase [MTRR; E.C.1.16.1.8]; aldose reductase [ALDR1; E.C.1.1.1.21]; aldehyde reductase [AKR1B10; E.C.1.1.1.2] and thioredoxin reductase [TXNRD; E.C.1.8.1.9]. Thus, the compounds of these embodiments can be utilized to detect any of the above enzymes.

In additional embodiments, the enzyme is a protease or peptidase and the compound comprises the structure:

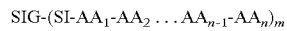

$$SIG-(SI-AA_1-AA_2\ldots AA_{n-1}-AA_n)_m$$

wherein each AA is independently an amino acid, n is an integer representing the total number of amino acids, wherein n is from 1 to about 200, and m is an integer from 1 to about 10; and wherein the protease or peptidase is capable of removing the amino acid sequence, allowing self-cleavage of the SI. Thus, although more than one amino acid is depicted in the above structure, these embodiments encompass the structures where there is only 1 amino acid (n=1). It is noted that in these embodiments, the amino acid sequence must be one that is a substrate for the particular protease or peptidase to be detected. Thus, the amino acid sequence for these compounds varies according to the specific requirements of the assayed protease or peptidase.

In more specific embodiments, the compound for detecting a protease or peptidase comprises the structure:

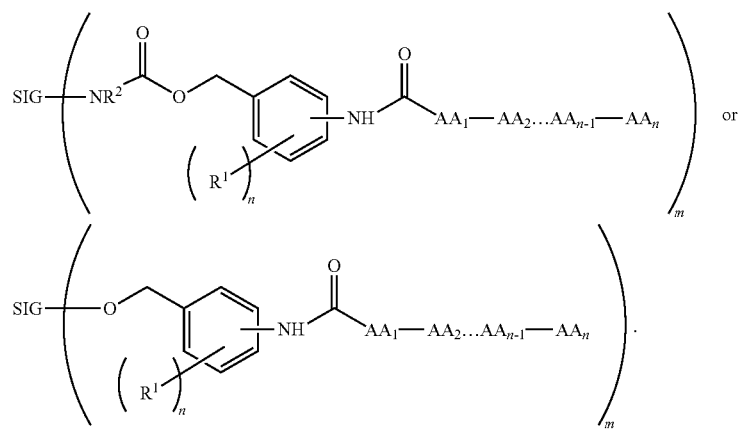

In a modification of the above peptidase-detecting embodiments, compounds are provided for detecting enzymes or non-enzymatic processes involved in addition or removal of a posttranslational modification of a protein. Nonlimiting examples of such enzymes include enzymes involved in acylation, alkylation, amidation, amino acid addition, diphthamide formation, gamma-carboxylation, glycosylation, glypiation, addition of a heme moiety, hydroxylation, iodination, attachment of nucleotide moiety, nitrosylation, S-glutathionylation, oxidation, phosphopantetheinylation, phosphorylation, pyroglutamate formation, sulfation, selenoylation, SUMOylation, or ubiquitination.

In some embodiments, the compound for detecting enzymes involved in a posttranslational modification comprises the structure:

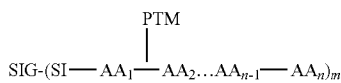

wherein each AA is independently an amino acid, PTM is a post-translational modification on any of the amino acids, n is an integer representing the total number of amino acids, wherein n is from 1 to about 200, and m is an integer from 1 to about 10; and wherein the enzyme involved in post-translational modification is capable of adding or removing the PTM, and, when the PTM is removed, a protease or peptidase is capable of removing the amino acid sequence, allowing self-cleavage of the SI. Thus, the detection of the enzyme involved in post-translational modification is a two-step process. In the first step, the enzyme, if present, adds or removes the PTM; in the second step a protease or peptidase is added, where, if the post-translational modification is not present, the protease or peptidase is able to remove the amino acid(s), releasing SIG, whereas if the post-translational modification is present, the protease or peptidase is unable to remove the amino acid(s) and SI remains bound to SIG, preventing the signal from being observed.

In more specific embodiments, the compound comprises the structure:

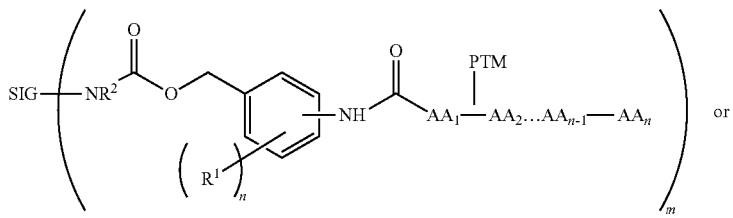

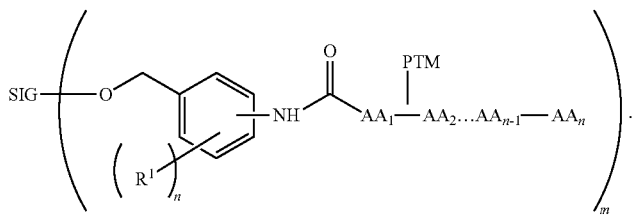

In a specific post-translational modification, the enzyme is a protein kinase. One structure useful for these embodiments comprises

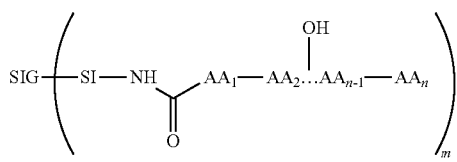

wherein —OH is a hydroxyl moiety on a serine, threonine, or tyrosine that is a target for phosphorylation by the kinase. It is noted that the amino acid sequence utilized in these embodiments must be one that is recognized by the particular protein kinase that is being detected.

In these embodiments, upon exposure to a protein kinase and ATP, the hydroxyl moiety becomes phosphorylated. With phosphorylation of the compound and subsequent addition of a protease or peptidase, the amino acids cannot be cleaved by the protease or peptidase, and SIG remains bound to SI, resulting in no signaling, whereas without phosphorylation of the compound, the protease or peptidase is able to remove the amino acids, resulting in the self-immolative removal of SI and release of a SIG that provides a signal. Thus, the assay associated with this kinase-detecting structure is a negative assay, since lack of kinase action results in a signal, whereas the presence of the kinase results in no signal.

More specific embodiments of the kinase-detecting compound comprise the structures:

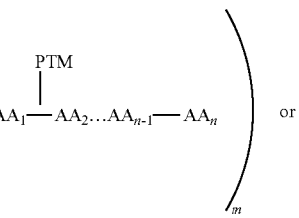

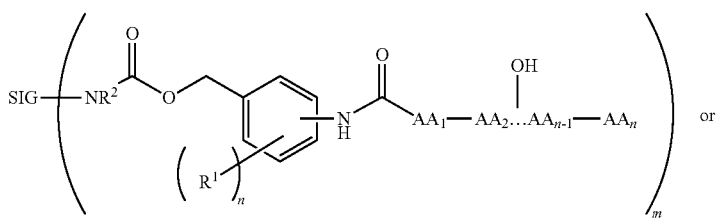

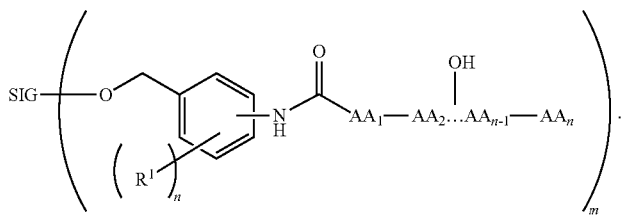

In another specific post-translational modification, the enzyme is a phosphatase. An exemplary compound for detecting the phosphatase comprises the structure:

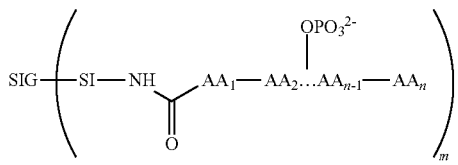

wherein —OPO$_3^{2-}$ is a phosphate moiety on a serine, threonine, or tyrosine that is a target for dephosphorylation by the phosphatase. It is noted that the amino acid sequence utilized in these embodiments must be one that is recognized by the particular phosphatase that is being detected. Such a phosphatase is detected with these compounds by combining the compound with a sample to be tested for the phosphatase then adding a protease or peptidase that is capable of removing the amino acids in the absence, but not in the presence, of the phosphate moiety. Thus, if the phosphatase is present in the sample, the phosphate group will be removed, allowing the protease or peptidase to remove the amino acids, resulting in the self-immolative removal of SI and release of a SIG that provides a signal. However, without a phosphatase in the sample, the phosphate group remains, preventing the protease or peptidase from removing the amino acids. SIG then remains bound to SI, resulting in no signaling.

More specific embodiments of the phosphatase-detecting compound comprise the structures:

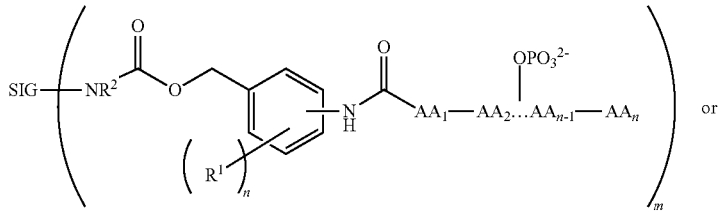 or

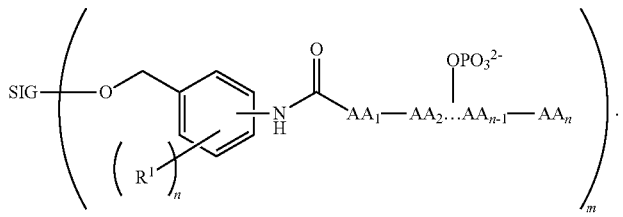

In yet another specific post-translational modification, the enzyme is a histone deacetylase (HDAC). An exemplary compound for detecting the HDAC comprises the structure:

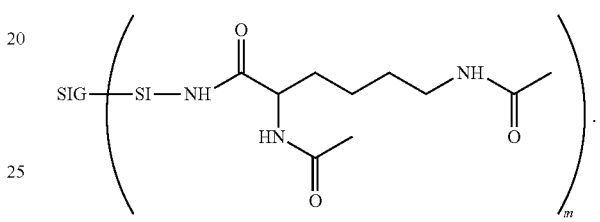

An HDAC is detected with these compounds by combining the compound with a sample to be tested for the HDAC then adding a protease or peptidase that is capable of removing the remaining amino acid in the absence, but not in the presence, of the acetyl moiety on the E-N-acetyl moiety. Thus, if the HDAC is present in the sample, the acetyl group will be removed, allowing the protease or peptidase to remove the amino acids, resulting in the self-immolative removal of SI and release of a SIG that provides a signal. However, without an HDAC in the sample, the acetyl group remains, preventing the protease or peptidase from removing the amino acids. SIG then remains bound to SI, resulting in no signaling.

More specific embodiments of the HDAC-detecting compound comprise the structures:

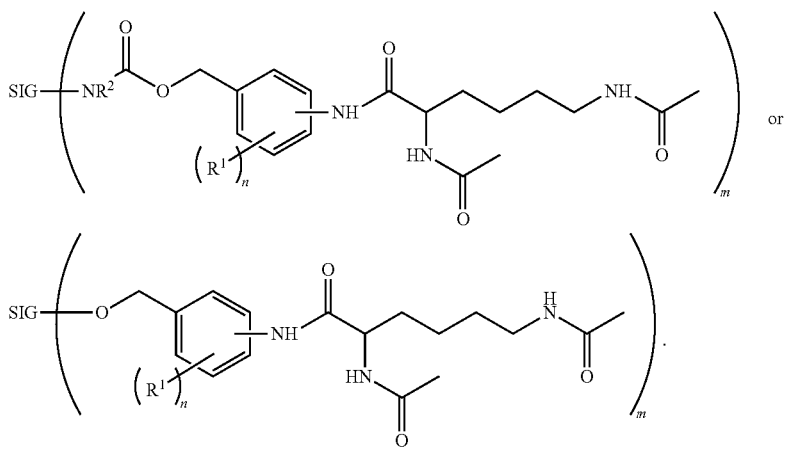

Examples of particular compounds that detect HDAC are

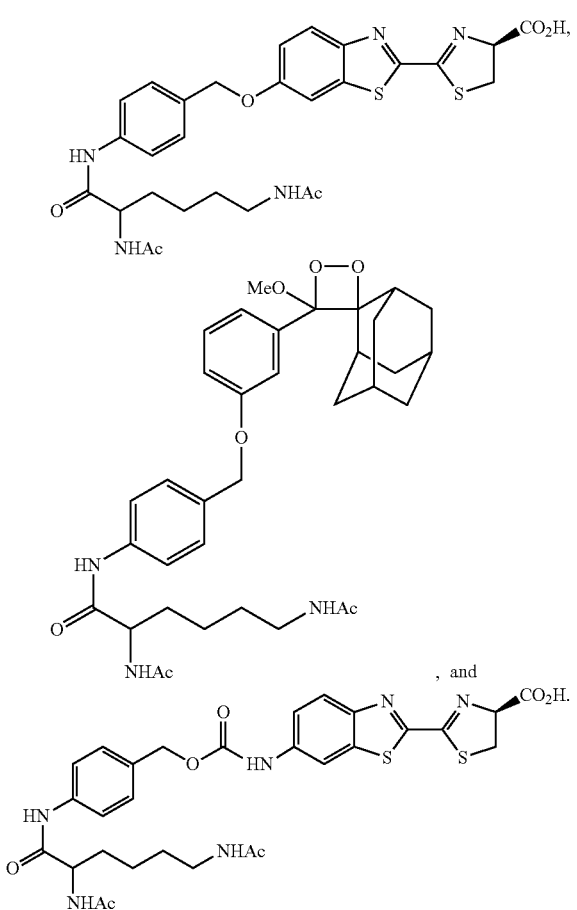

The above compounds are useful in methods of detecting an activator. Thus, in some embodiments, a method of determining whether a sample comprises an activator is provided. The method comprises (a) incubating the sample with the above-identified compound for a time and under conditions sufficient for MOD to be modified by the activator; and (b) determining whether SIG generates a greater signal than the signal generated by the compound without the activator. In these embodiments, a greater signal indicates that the sample comprises the activator.

These methods are useful for detection of the activator in any sample. In some embodiments, the sample is a fluid of an organism or a colony of organisms, or an extract thereof. In some aspects of these embodiments, the organism or colony of organisms is microorganisms, for example a prokaryote or an archaea, or a eukaryotic microorganism such as a protist. In other aspects, the organism is a multicellular eukaryote. In some of these embodiments, the sample is an extract of a cell, tissue or organ of the multicellular organism. The eukaryote multicellular organism can be a mammal or any other eukaryote.

In some embodiments, the sample for these methods comprises a living cell, i.e., a prokaryotic, archaeal or eukaryotic cell, e.g., from a mammal, for example a human.

The activator for these methods can be any activator capable of acting on MOD and initiating the self-immolative cleavage of the SI from SIG. In some embodiments, the activator is a disulfide reducing agent. Exemplary compounds for detecting such an activator is provided above. Particular disulfide reducing agents that can act as activators include glutathione, cysteine or homocysteine.

In various embodiments of these methods, the activator is an enzyme, e.g., a nitroreductase, a kinase, an aminopeptidase, an esterase, a lipase, a protease, a peptidase, a phosphatase, a sulfatase, a sulfotransferase, a carboxylase, a decarboxylase, a glycosylase, an amidase, a deamidase, an aminase, a deaminase, an acetyltransferase, a methylase, a deacetylase, a demethylase, or an acetylase.

In some of these methods, the enzyme is a lipase or esterase. Exemplary compounds useful to detect a lipase or esterase are provided above.

In other embodiments of these methods, the enzyme is a nitroreductase. Exemplary compounds for detecting nitroreductases are also provided above.

In additional embodiments of these methods, the enzyme is a protease or peptidase. Examples of compounds useful for detecting proteases are further provided above.

The enzyme for these methods can also be an enzyme involved in addition or removal of a posttranslational modification of a protein. See above for exemplary compounds useful for these methods. In one aspect of these embodiments, the enzyme is a protein kinase. As discussed above, the sample is also incubated with a peptidase either during or after the incubation step (a), but before the determining step (b). As further discussed above, the signal in these methods is an inverse signal such that increased activation of SIG indicates a decrease in the amount of protein kinase in the sample. In another aspect of these embodiments, the enzyme is a phosphatase. As discussed above, the sample is also incubated with a peptidase either during or after the incubation step (a), but before the determining step (b). In an additional aspect of these embodiments, the enzyme is a histone deacetylase. As also discussed above in relation to the histone deacetylase compounds, the sample is also incubated with a peptidase either during or after the incubation step (a), but before the determining step (b).

Also provided herewith is a method of determining whether a cell comprises a nitroreductase. The method comprises (a) incubating the cell with any of the above-described compounds that are useful for detecting a nitroreductase, for a time and under conditions sufficient for the compound to enter the cell and be exposed to a nitroreductase if present in the cell; and (b) determining whether SIG generates a greater signal than the signal generated by the compound when not exposed to a nitroreductase. In these methods, a greater signal indicates that the cell comprises the nitroreductase. Examples of these assays are described in Examples 6-12 below.

In these methods, the cell can be incubated with the compound for any length of time, e.g., more than about 120 minutes, about 120 minutes or less, about 60 minutes or less, or about 30 minutes or less. Shorter incubation times (e.g., 10 minutes or less, 5 minutes or less, or 2 minutes or less) are sufficient where the nitroreductase is not in a cell. See, e.g., FIG. 2.

The cell in these embodiments can be any cell of any microorganism, for example a mammalian cell, or the cell of a microorganism, for example a bacterium.

This method can be used to identify any enzyme having nitroreductase activity, including DT-diaphorase [NQO1; E.C.1.6.99.2]; cytochrome P450-reductase [CYPOR; E.C.1.6.2.4]; inducible nitric oxide synthase [NOS2A; E.C.1.14.13.39]; cytochrome B5 reductase [DIAL; E.C.1.6.2.2]; xanthine oxidase [XO; E.C.1.17.3.2]; xanthine dehydrogenase [XDH; E.C.1.17.1.4]; adrenodoxin oxidoreductase [FDXR; E.C.1.18.1.2]; methionine synthase reductase [MTRR; E.C.1.16.1.8]; aldose reductase [ALDR1; E.C.1.1.1.21]; aldehyde reductase [AKR1B10; E.C.1.1.1.2] or thioredoxin reductase [TXNRD; E.C.1.8.1.9].

In various embodiments of these methods, SIG is a chemiluminescent dye or a fluorophore. Particular compounds useful for these methods include

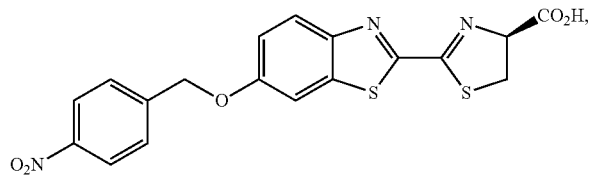

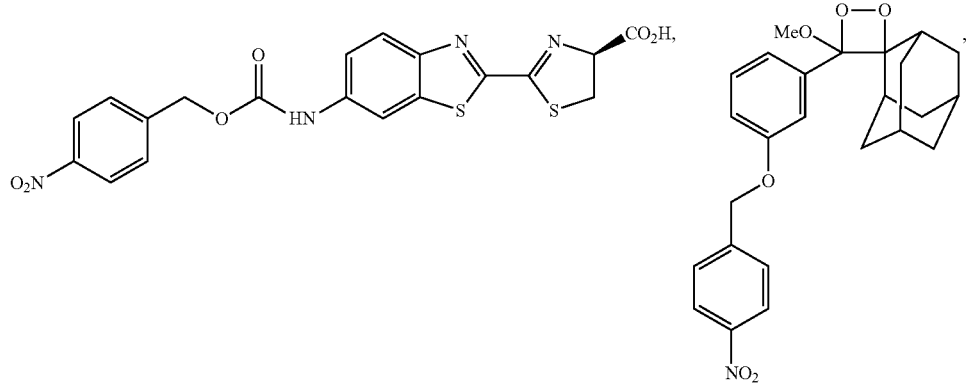

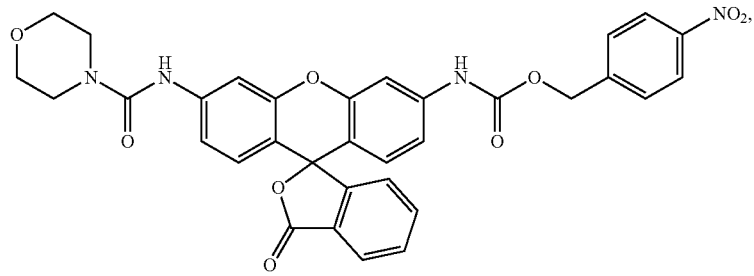

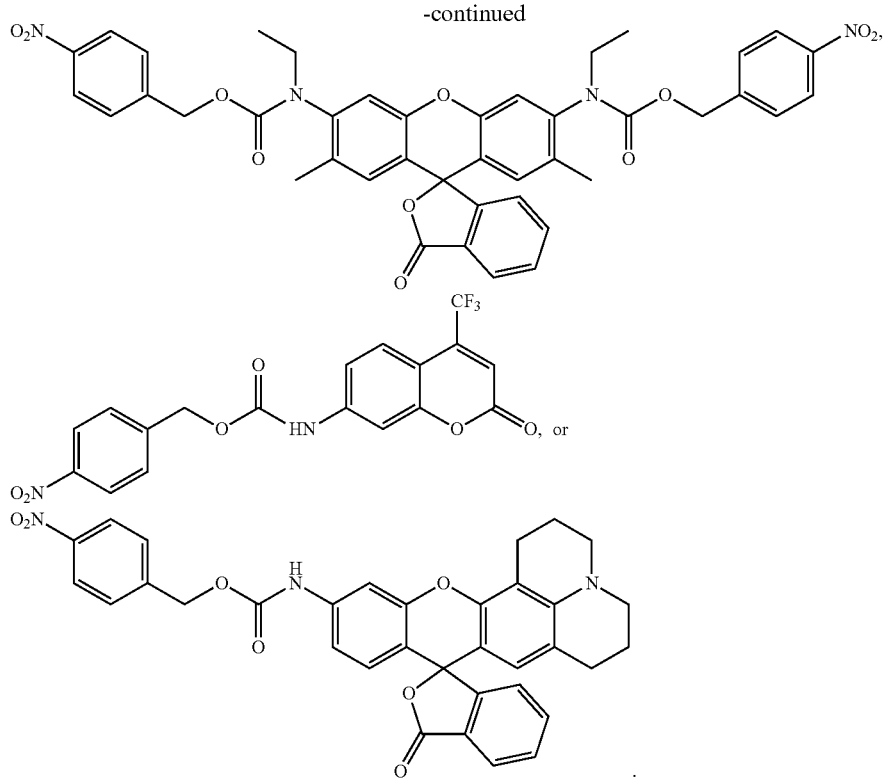

This method can also be used with microorganisms, e.g., bacteria, to determine whether cells of the microorganism produce nitroreductase. Such methods are useful in identifying or characterizing microorganisms, e.g., that are in a tissue or fluid sample of a vertebrate infected with the microorganism or in an environmental sample.

Additionally, this method can be used to identify nitroreductase in a sample, by incubating the sample with any of the above-identified compounds, then determining whether fluorescence or luminescence of the compound increases during the incubation. In this method, an increase in fluorescence or luminescence during the incubation indicates that the sample comprises a nitroreductase. In some embodiments, the nitroreductase is quantified in the sample by comparing the fluorescence or luminescence of the compound after the incubation with fluorescence or luminescence of a known quantity of nitroreductase incubated with the compound under the same conditions.

These methods for detecting nitroreductase in cells are particularly useful for detecting hypoxia in cells, for example in tumor cells. The tumor microenvironment is one of the most critical factors in tumor progression and cancer treatment outcome. The presence of either transiently or chronically hypoxic cells constitutes an important characteristic of solid tumors since low oxygen levels are not usually present in tissues under physiological conditions. A correlation exists between the percentage of hypoxic cells in the solid tumor and cancer treatment prognosis since hypoxic cells are refractory to radiation therapy and resistant to toxic drugs used in chemotherapy. As a result, detection and analysis of hypoxic cell fractions in tumors can provide invaluable information about cancer status, its prognosis and insight into the specific treatment options.

Detection of hypoxic cells also plays a role in research areas outside of cancer. Such areas include studies of reactive oxygen and nitrogen species, ageing, apoptosis, autophagy, cardiac and pulmonary ischemia, neurodegenerative and immunological disorders.

Various techniques have been used to measure cell oxygenation status. Some of those techniques, such as oxygen microelectrodes, histomorphometric analysis or determination of DNA strand breaks, are invasive and/or use equipment not readily available for investigators. Other techniques are based on the hypoxia-induced reduction of a labeled 2-nitroimidazole. Labels used in this context include $^{14}C$, $^{3}H$, $^{19}F$, $^{75}Br$, $^{76}Br$ and $^{77}Br$ employed in NMR, PET, autoradiography and immunohistochemistry. Fluorescent or luminescent dyes are an attractive alternative option since they are sensitive, environmentally safe and they can be used in non-invasive assays. As is known, mammalian nitroreductases require anaerobic conditions for activity. Thus, fluorescent or luminescent dyes that are activated by nitroreductase provide a good approach for measuring oxygen status of mammalian cells.

Besides measurement of hypoxia fluorescent or luminescent dyes activated by nitroreductase can be employed in order to detect several pathogenic microorganisms producing nitroreductases. Additionally, the ability of nitroreductase to reduce nitro groups has been exploited as part of a reporter gene assay that employs the red carbocyanine dye CytoCy5S. This squaraine carbocyanine structure contains a 3,5-dinitrophenyl substituent that essentially quenches the fluorescence at long wavelengths. Upon enzyme activity, however, the nitro-groups are reduced to hydroxylamines (and presumably amino-groups) intracellularly. This relieves the quenching and results in an increase in fluorescence. The substrate has been further modified to make it into the di-ethyl ester for membrane permeability. These ethyl esters are removed by intracellular esterase activity so that the fluorescent end-product is well retained within the cell. The assay therefore uses this 'red-shifted' excitation and emission (excitation 647 nm emission 667 nm) for the reporter gene assays which allows use with other fluorescent reporters, such as green fluorescent protein (GFP), to be used in the same cell. Expression of nitroreductase has been demonstrated in a number of mammalian cells without reported toxicity.

For a fluorescent marker to be suitable for determining hypoxic conditions, it should meet several conditions. First, it should have favorable excitation and emission wavelengths, and as a result be excitable and detectable by readily available light sources and filter systems. Second, it should have a high quantum yield and high molar absorption coefficient. Third, it should exhibit a significant fluorescence difference between the hypoxic and the normoxic forms of the dye to maximize the signal-to-background ratio.

Several dyes have been described for which the fluorescence increases upon the activation by nitroreductases. US Patent Publication US2002/0031795 A1 describes a group of non-fluorescent 7-nitrocoumarins that are reduced by nitroreductase to fluorescent species, and are used for the detection of microbial infection. Additional nitrocoumarin compounds are provided in US Patent Publication US2010/0173332. Also, PCT Publication WO 2008/030120 describes chemically diversified non-fluorescent probes that are reduced in the presence of nitroreductase to form fluorescent derivatives. Additionally, a fluorogenic substrate which can detect the activity of certain enzymes that reduce nitro compounds to amines and inorganic nitrates, 6-Chloro-9-nitro-5-oxo-5H-benzo[a]phenoxazine ("CNOB", Invitrogen) has been developed. Although the compound is a good substrate for some bacterial nitroreductases it is apparently not a substrate for mammalian counterparts. The compound lacks stability in culture medium under conditions of low oxygen, making it unsuitable as a probe for mammalian single-electron reductases which require anaerobic conditions for activity. Nitro group quenched cyanine dyes are also taught in US Patent Publication US2003/0186348A1, U.S. Pat. No. 7,579,140 B2, and U.S. Pat. No. 7,662,973 B2. Those dyes detect microbial nitroreductases in connection with reporter gene applications. The above-described compounds, however, generally have considerable fluorescence in their quenched, unreduced form. Upon the action of nitroreductase a modest 3-4-fold enhancement of the fluorescence is observed, offering a limited dynamic range of quantification.

Nitro-substituted squaraine reporter dyes and the methods of using such dyes for detection of nitroreductase enzyme activity and nitroreductase gene expression in cellular assays are disclosed in US Patent Publication US2008/0317674. However, the majority of the compounds described therein contain a nitroreductase-sensing nitrobenzyl appendage which is non-conjugated to the dye structure, and therefore generate rather modest fluorescence enhancement upon activation by the enzyme.

Thus, the present invention is also directed to a method of determining whether a mammalian cell is hypoxic. The method comprises (a) incubating the cell with the above-identified compound for a time and under conditions sufficient for the compound to enter the cell and be exposed to a nitroreductase if present in the cell, where the nitroreductase is indicative of hypoxia in the cell; and (b) determining whether the signal of the compound in the cell increases during the incubation. In this method, an increase in the signal intensity during the incubation indicates that the cell is hypoxic.

When using this method with cells, e.g., mammalian cells to determine whether the cells are hypoxic, the method can be combined with the use of dyes for determining other characteristics of the cell. In some of these embodiments, oxidative stress in the cell is also determined, by including a probe that detects reactive oxygen species in the incubation step (a), then determining whether the probe detects reactive oxygen species in the cell, where the presence of reactive oxygen species indicates oxidative stress in the cell. Any probe that detects reactive oxygen species can be used here, for example 2',7'-dichlorofluorescein diacetate, dihydrorhodamine 123, 3'-(p-aminophenyl)fluorescein (APF), 3'-(p-hydroxyphenyl)fluorescein (HPF), aminophenoxycalcein (APC), mitoAR, mitoHR, DPAX, DMAX, dihydroethidium, or the probes described in U.S. Patent Publications US2010/0081159 and US2009/0253118. See also Tarpey et al., 2004; and Nagano, 2009. Examples of reactive oxygen species that can be detected by these methods include superoxide ($O_2.^-$), hydroperoxy ($HO_2.$), hydrogen peroxide ($H_2O_2$), peroxynitrite ($ONOO^-$), hypochlorous acid (HOCl), hypobromous acid (HOBr), hydroxyl radical (HO.), peroxy radical (ROO.), alkoxy radical ($R^O.$), singlet oxygen ($^1O_2$), lipid peroxides, lipid peroxyradicals or lipid alkoxyl radicals, and combinations thereof.

In other embodiments, the method for determining nitroreductase activity and/or hypoxia in a cell further comprises determining the nitrative stress in the cell, by including a probe that detects reactive nitrogen species in the incubation step (a), then determining whether the probe detects reactive nitrogen species in the cell, where the presence of reactive nitrogen species indicates nitrative stress in the cell. Examples of useful probes for this method include diaminoanthraquinone, diaminonaphthalene, a diaminofluorescein, a diaminorhodamine, a diaminocyanine, an NiSPY, dichlorodiaminocalcein, DAMBO-$P^H$ and the probes described in U.S. Patent Publications US2010/0081159 and US2009/0253118. See also Ueno et al., 2006. Examples of reactive nitrogen species that can be detected in these methods include nitric oxide (NO), nitrogen dioxide radical ($NO_2$), peroxynitrite anion ($ONOO^-$), peroxynitrous acid (ONOOH), nitrosoperoxycarbonate anion ($ONOOOCO_2^-$), nitronium cation ($NO_2^+$), nitrosonium cation ($NO^+$) or dinitrogen trioxide ($N_2O_3$), and combinations thereof.

In additional embodiments, the method for determining nitroreductase and/or hypoxia in a cell further comprises determining the halogenating stress in the cell, by including a probe that detects reactive halogen species in the incubation step (a), then determining whether the probe detects reactive halogen species in the cell, where the presence of reactive halogen species indicates halogenating stress in the cell. Examples of such probes include those described in U.S. Patent Publications US2010/0081159 and US2009/0253118, and Matthew and Anastasio, 2006; and Anastasio and Matthew, 2006. Examples of reactive halogen species that can be detected by these methods include hypochlorous acid (HOCl), hypochlorite ion ($ClO^-$) monochloramine ($NH_2Cl$), chlorine dioxide ($ClO_2$), nitryl chloride ($NO_2Cl$), chlorine ($Cl_2$), bromine ($Br_2$), bromochloride (BrCl), hypobromous acid (HOBr), hypobromite ion ($BrO^-$) or bromamine species, and combinations thereof.

In further embodiments, the method for determining nitroreductase and/or hypoxia in a cell further comprises determining the presence of a membrane transporter MDR1, MRP or BCRP in the cell, by including at least one xanthene compound that is transportable across a cell membrane by the membrane transporter in the incubation step (a), then determining whether the at least one xanthene compound is excluded from the cell, where the exclusion of the xanthene compound from the cell is indicative of the presence of the membrane transporter. See, e.g., U.S. patent application Ser. No. 12/799,853, filed May 3, 2010. The presence of the membrane transporter in the cell may indicate that the cell is resistant to a chemotherapeutic agent. In some embodiments, this method further comprises comparing the exclusion of the xanthene compound from the cell with the exclusion of the xanthene compound from a comparable cell treated with the xanthene compound and a membrane transporter inhibitor.

In still other embodiments, the method for determining nitroreductase and/or hypoxia in a cell further comprises determining the location of a subcellular organelle in the cell, by including at least one dye that localizes to the organelle in the incubation step (a), then visualizing the location of the organelle by visualizing the at least one dye. See, e.g., U.S. Pat. Nos. 7,569,695 and 7,737,281 and U.S. Patent Publications US2009/0336954, US2010/0068752, US2010/0062460, and US2010/0093004. As discussed in those publications, the organelle may be, e.g., the cell nucleus, the endoplasmic reticulum or the mitochondria. Additionally, the dye may be a cationic amphiphilic tracer compound that localizes to a vacuole in a cell. An excess above normal accumulation of vacuoles within the cell can be indicative of a lysosomal storage disease.

As indicated in Example 6, hydrosulfite is a reducing agent that mimics nitroreductases in that it is capable of reducing the nitro moiety on the nitroreductase probes discussed above. Hydrosulfites, in particular sodium hydrosulfite, are sometimes used in food as a preservative. However, its use in foods is a concern due to its ability to cause acute allergic reactions in sensitive individuals. It is therefore useful to test for hydrosulfites in foods. The nitroreductase probes can be used for that purpose.

Thus, the present invention is also directed to a method of detecting hydrosulfite in a sample, the method comprising (a) combining the sample with any of the above-described compounds that detect nitroreductases, then (b) determining whether SIG generates a greater signal than the signal generated by the compound when not exposed to a hydrosulfite. In these embodiments, a greater signal indicates that the sample comprises a hydrosulfite.

In some embodiments of this method, the hydrosulfite is sodium hydrosulfite.

The sample for these methods can be any sample suspected of containing a hydrosulfite. In some embodiments, the sample is a food.

Preferred embodiments are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the examples.

Example 1

Synthesis of CD-1 a). Preparation of Intermediate CD-2

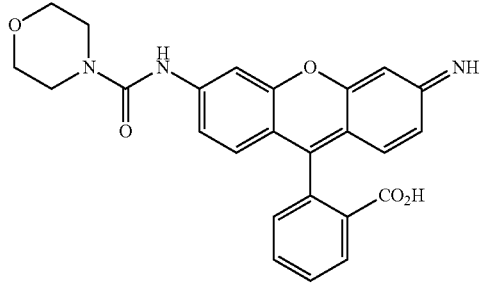

CD-2

To a solution of 500 mg Rho110 in dimethylformamide, 290 μl of N,N'-diisopropylethylamine was added and the mixture was stirred on ice for 10 minutes. Then 160 μl of N-morpholinecarbonyl chloride was added dropwise. The reaction mixture was stirred on ice for an additional 15 minutes and then at room temperature for 2 days. The reaction mixture was evaporated to dryness and the oily residue was dissolved in chloroform containing a small amount of methanol. The product was purified on a Biotage SP4 System with a SNAP 100 g column and a chloroform methanol gradient.

b). Preparation of CD-1

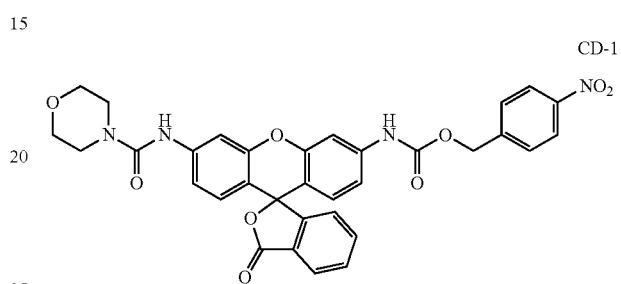

CD-1

To 23 mg of intermediate CD-2 dissolved in a mixture of dichloromethane (1 ml) and pyridine (1 ml), 40 mg of p-nitrobenzyl chloroformate in chloroform was added dropwise. The solution was stirred at room temperature for 2 days and the solvent was removed in vacuo. The resin was co-evaporated with toluene, dissolved in chloroform and purified on a Biotage SP4 System with a SNAP 25 g column and a chloroform methanol gradient, to give 10 mg of a white product.

Example 2

Synthesis of CD-3

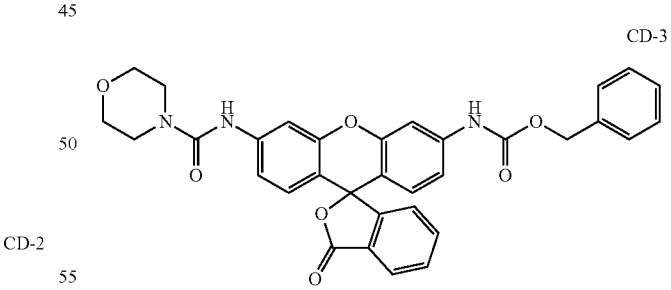

CD-3

To 22 mg of CD-2 in the mixture of dichloromethane (0.7 ml), methanol (0.15 ml) and pyridine (1 ml), a solution of benzyl chloroformate (24 mg) in chloroform was added dropwise. The reaction mixture was stirred at the room temperature for 3 days and the solvent was removed in vacuo. The resin was co-evaporated with toluene, dissolved in chloroform and purified on a Biotage SP4 System with a SNAP 25 g column and a chloroform methanol gradient, to give off-white crystals.

Example 3

Synthesis of CD-4

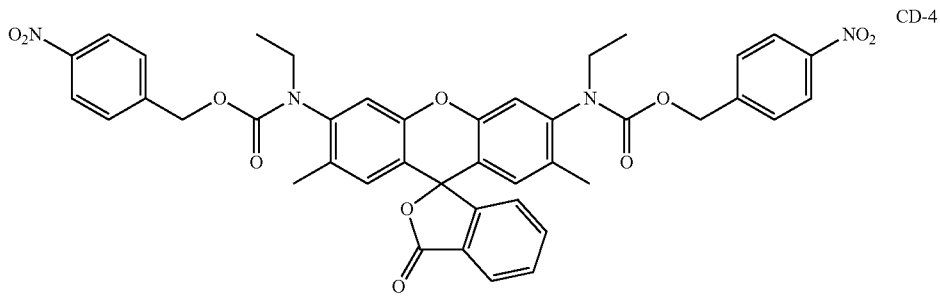 [SMILES: CCN(C(=O)OCc1ccc([N+](=O)[O-])cc1)c1cc2c(cc1C)C1(OC(=O)c3ccccc31)c1cc(C)c(N(CC)C(=O)OCc3ccc([N+](=O)[O-])cc3)cc1O2]

To 50 mg of Rho575 in dimethylformamide, 53 µl of N,N'-diisopropylethylamine was added followed by 78 mg of p-nitrobenzyl chloroformate dissolved in dimethylformamide. The reaction mixture was stirred for 3 days and the solvent was removed in vacuo. The residue was dissolved in chloroform and purified on a Biotage SP4 System with a SNAP 25 g column and a chloroform methanol gradient, to give a pink product.

Example 4

Synthesis of CD-5

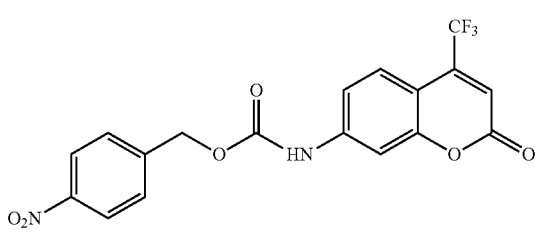

To 46 mg of 7-amino-4-trifluoromethylcoumarin in 250 µA of dichloromethane, 300 µl of pyridine was added followed by 2.5 equivalents of p-nitrobenzyl chloroformate dissolved in 250 µl of dichloromethane. The reaction mixture was allowed to stir at room temperature overnight and another 2.5 equivalents of p-nitrobenzyl chloroformate dissolved in dichloromethane were added. After 2 days the solvent was removed in vacuo and the residue was coevaporated several times with toluene. The resulting mixture was dissolved in dichloromethane and purified on a Biotage SP4 System with a SNAP 25 g column and a dichloromethane methanol gradient, to give an off-white product.

Example 5

Synthesis of CD-6 a). Preparation of CD-7

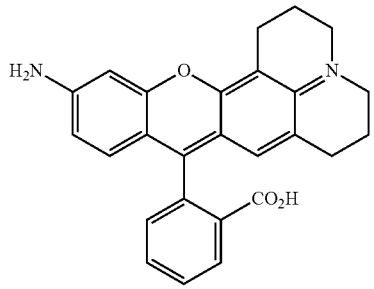

To a mixture of 55 mg 3-aminophenol, 95 mg 8-hydroxyjulolidine and 75 mg phthalic anhydride in 0.5 ml of DMF, a catalytic amount of anhydrous zinc chloride was added. The reaction mixture was irradiated in a microwave oven in a closed vessel, at 100 W and 120° C. for 60 minutes, then evaporated to dryness. The solid residue was dissolved in chloroform containing a small amount of methanol. The product was purified on the Biotage SP4 System with a SNAP 50 g column and a chloroform methanol gradient.

b). Preparation of CD-6

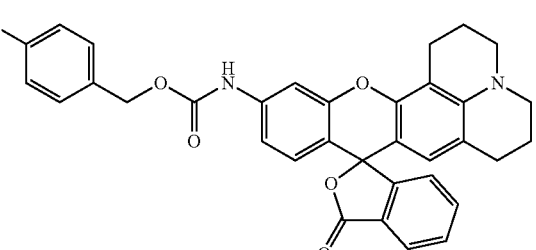

To 30 mg of CD-7 in dimethylformamide, 32 µl of N,N'-diisopropylethylamine was added followed by 47 mg of p-nitrobenzyl chloroformate dissolved in dimethylformamide. The reaction mixture was allowed to stir for 3 days and the solvent was removed in vacuo. The residue was dissolved in chloroform and purified on Biotage SP4 System with SNAP 25 g column and chloroform methanol gradient to give off-white product.

Example 6

Nitroreductase Assays (a) Chemical Assay

Figure 2:
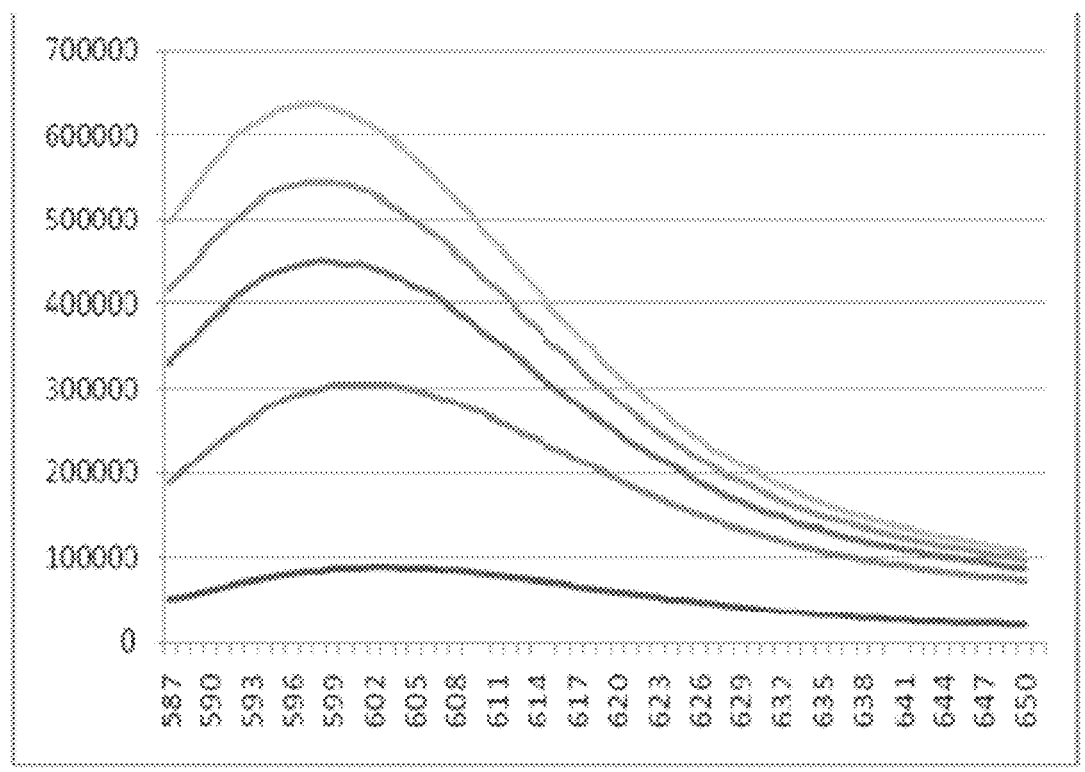
FIG. 2 is a graph illustrating fluorescence enhancement of compound CD-6 as a function of time. The lines represent fluorescence intensity at 0, 1, 5, 15 and 60 minutes after induction by sodium hydrosulfite solution.
Figure 3A:
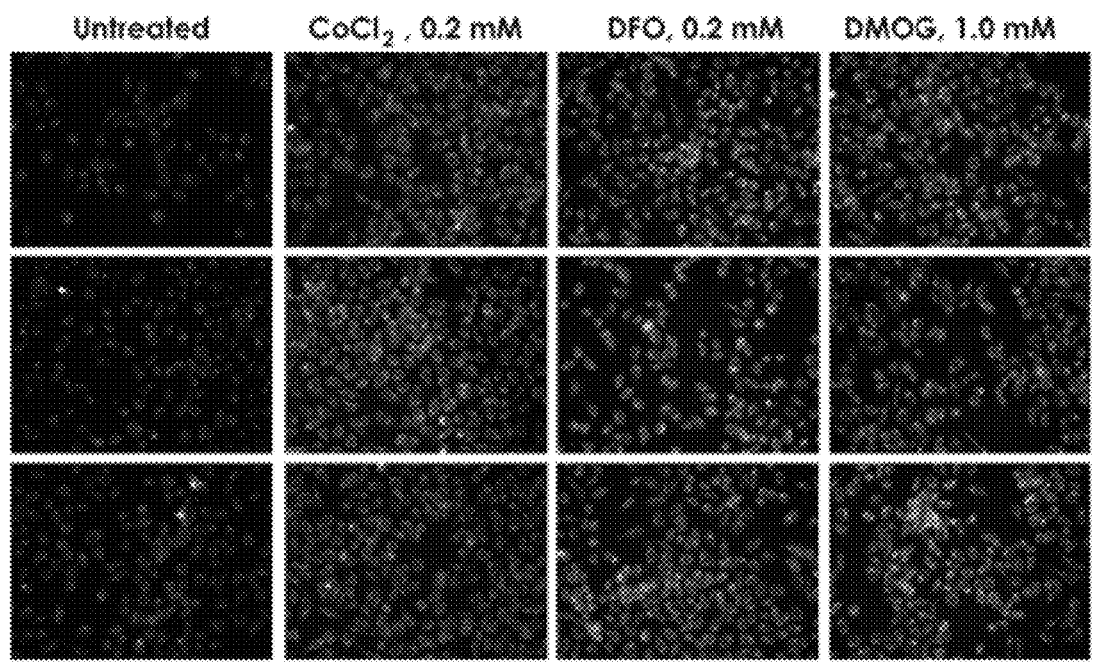
FIG. 3 is fluorescence micrographs showing compound CD-1 detection of hypoxic HeLa cells post chemical hypoxia induction and post-anoxia treatment, while control compound, CD-3, lacking a p-nitro group, is inactive in the live cells at the above conditions. Panel A shows HeLa cells that were seeded on the glass slides and treated the next day with 5 μM of CD-1 (probe). Hypoxia was induced chemically as described in Example 6. After 3.5 h, cells were washed with PBS, coverslipped and observed using a fluorescence microscope with FITC filters, 490ex/525em. Panel B shows HeLa cells that were seeded on the glass slides and treated the next day with 5 μM of CD-3 (control). Hypoxia was induced chemically as described in Example 6. After 3.5 h, cells were washed with PBS, coverslipped and observed using a fluorescence microscope with FITC filters, 490ex/525em. Panel C shows HeLa cells that were seeded on the glass slides and treated the next day with 5 μM of CD-1 (Probe) or CD-3 (Control). Cells were subjected to anoxic conditions (95% of $N_2$, 5% of $CO_2$) as described in Example 6. After 3.5 h, cells were washed with PBS, coverslipped and observed using fluorescence microscope with FITC filters, 490ex/525em. Panel D shows HeLa cells that were seeded on the glass slides and treated the next day with 0.2 M pimonidazole. Cells were subjected to anoxic conditions (95% of $N_2$, 5% of $CO_2$) as described in Example 6. After 3.5 h, cells were washed with PBS, coverslipped and observed using a fluorescence microscope with FITC filters, 490ex/525em.
Figure 3B:
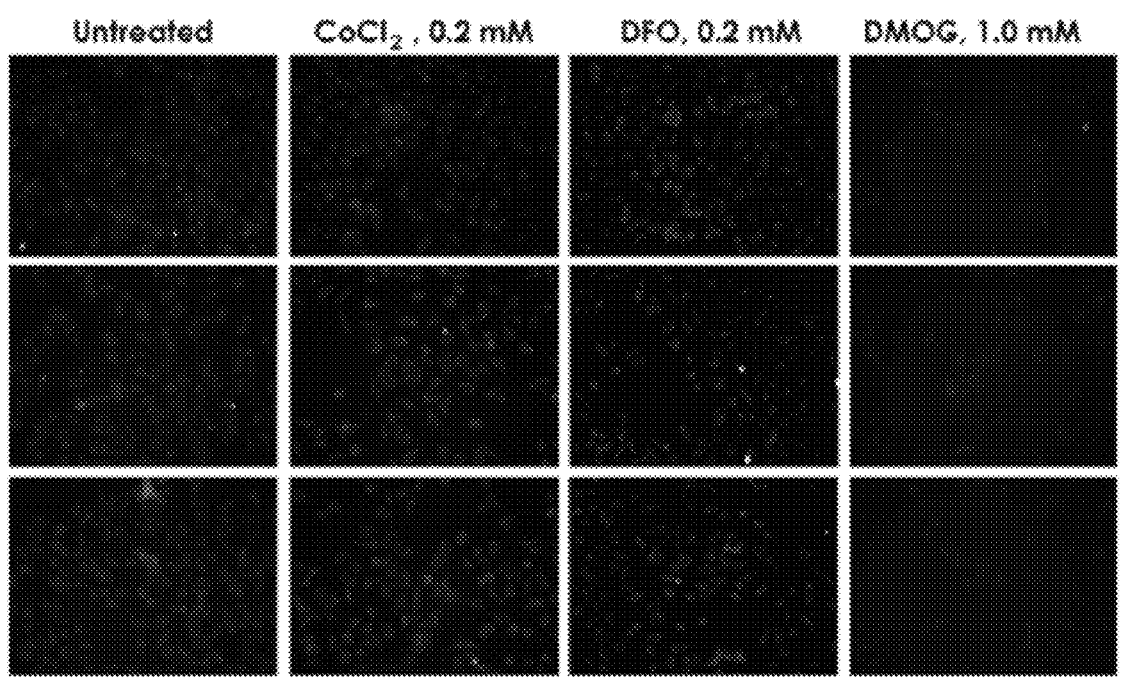
Figure 3C:
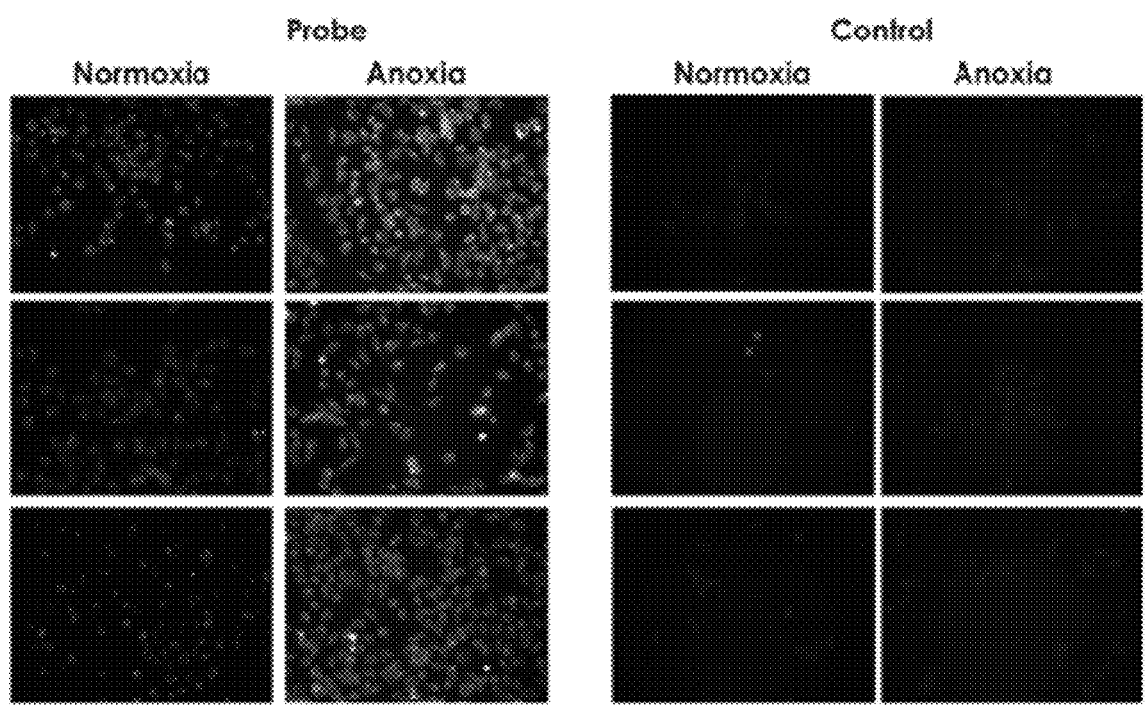
Figure 3D:
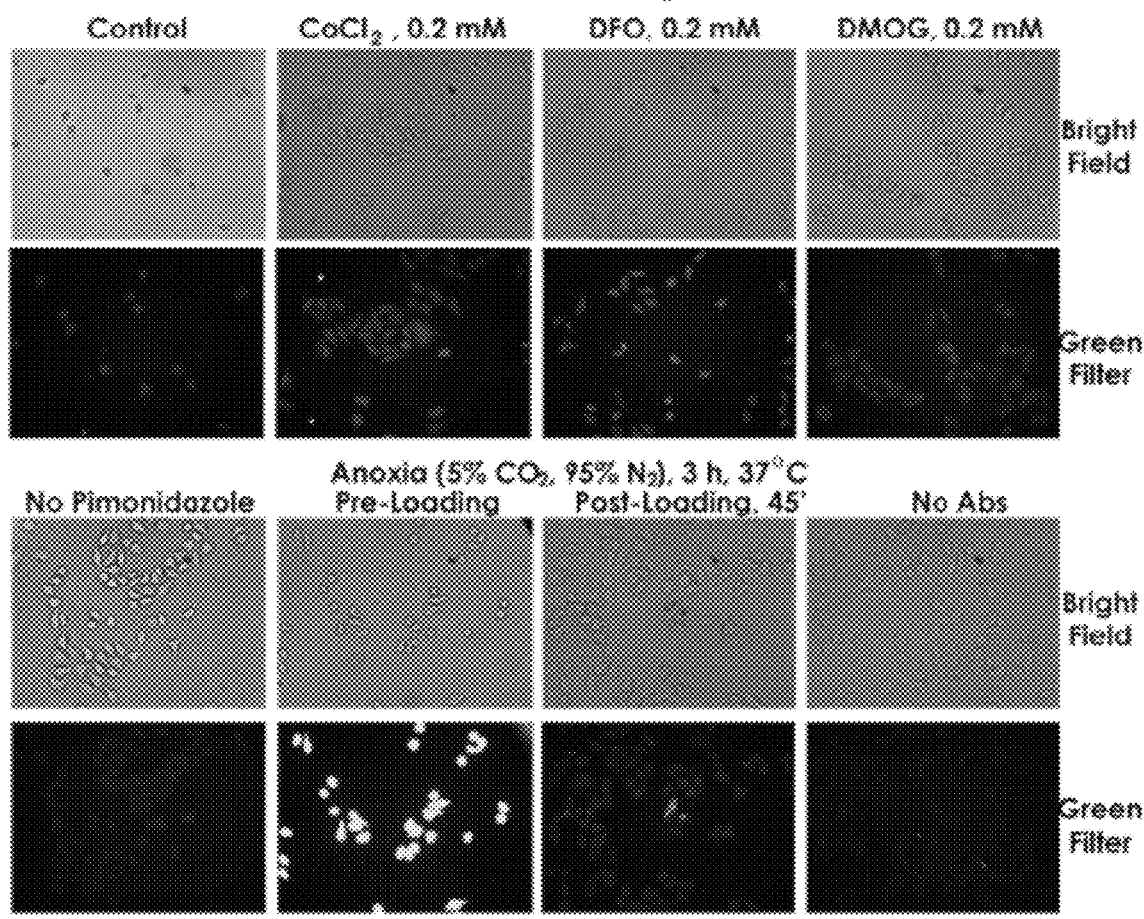
Figure 4A:
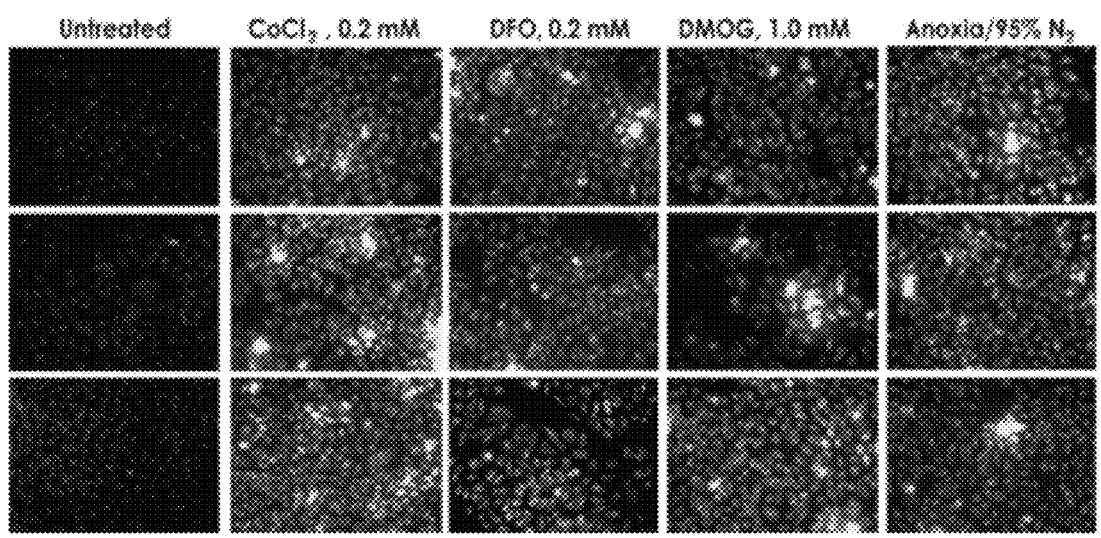
FIG. 4 is fluorescence micrographs of hypoxic HeLa cells with hypoxic probes CD-1, CD-4, CD-5 or CD-6. HeLa cells were seeded on the glass slides and treated the next day with a self-immolative hypoxia probe. The following probes were employed: CD-5 (5 μM, Panel A), CD-1 (5 μM, Panel B), CD-4 (1 μM, Panel C), CD-6 (1 μM, Panel D). Hypoxia was induced chemically as described in Example 7. After 3.5 h incubation, cells were washed with PBS, coverslipped and visualized using an Olympus BX-51 fluorescence microscope with a DAPI filter set (350 ex/470em) for CD-5, an FITC filter set (490ex/525em) for CD-1, an orange filter set (550ex/620em) for CD-4 and a Texas Red filter set (596ex/670em) for CD-6.
Figure 4B:
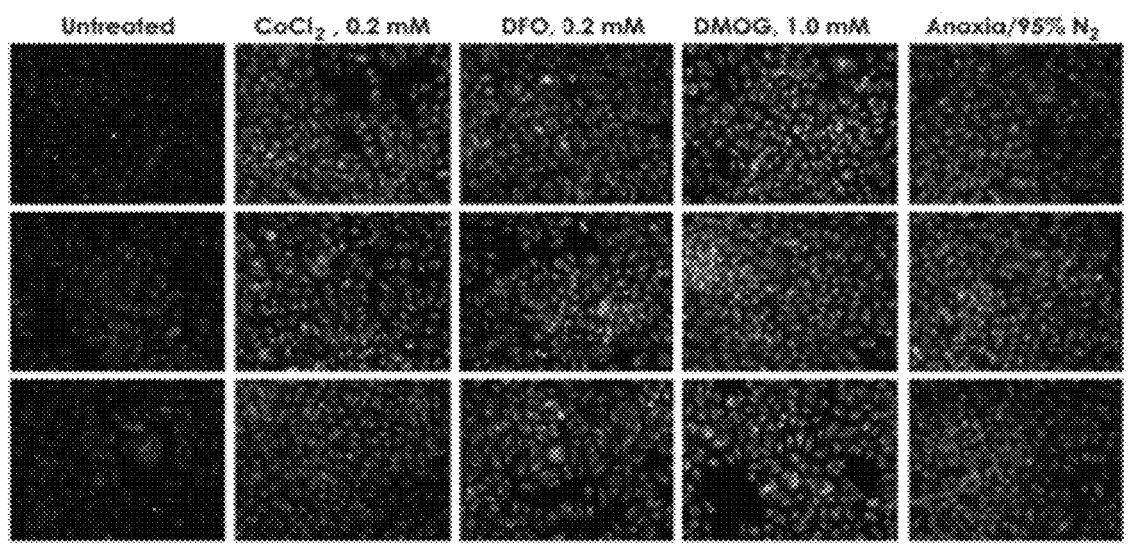
Figure 4C:
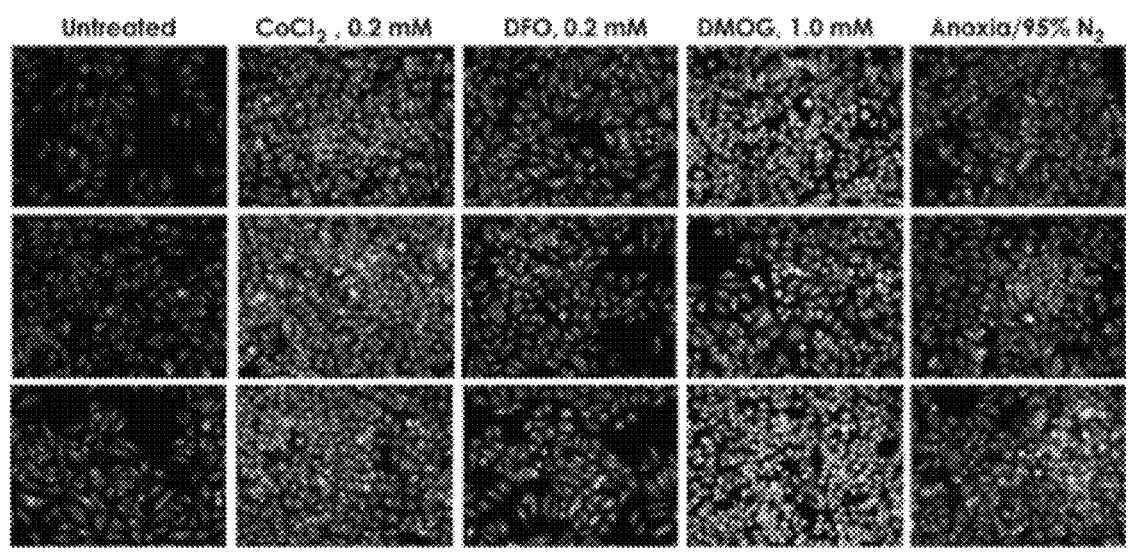
Figure 4D:
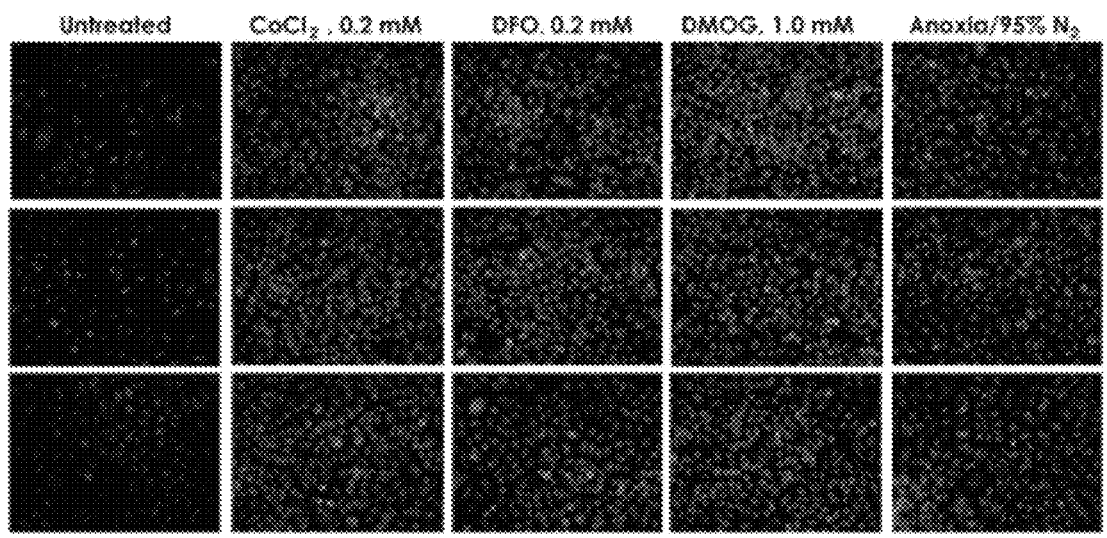

A solution of probe CD-6 in DMSO (0.1-1.0 μl) was added to 90 μl of PBS buffer (10 mM, pH 7.4). After mixing, 10 μl of 100 mM aqueous sodium hydrosulfite was added. The reaction mixture was incubated at room temperature for amount of time ranging from 1 minute to 6 hours. As a control, 10 μl of water instead of sodium hydrosulfite was used. FIG. 2 illustrates increasing fluorescence of CD-6 over a 60 minute period after combining with sodium hydrosulfite.

(b) Enzymatic Assay

E. coli nitroreductase (Sigma-Aldrich, St. Louis, Mo.) at 10 mg/ml was incubated in PBS buffer (pH 7.4) with a DMSO solution of a given hypoxia marker in the presence of 500 μM NADH (Sigma-Aldrich, St. Louis, Mo.). The incubation was carried out at 37° C. for 1 h. Small samples of the reaction mixture were taken for spectral analysis at several time points (typically at 5, 15, 30 and 60 min).

Example 7

Detection of Hypoxia with Hypoxia Markers Using Fluorescence Microscopy

The human cervical adenocarcinoma epithelial cell line HeLa, U-2 OS human bone osteosarcoma cell line and hamster ovary CHO K1 cell line were obtained from ATTC. HeLa cells were routinely cultured in Eagle's Minimum Essential Medium with low glucose (ATCC), supplemented with 10% fetal bovine serum (ATCC) and 100 U/ml penicillin, 100 μg/ml streptomycin (Sigma-Aldrich, St. Louis, Mo.). U-2 OS cells were routinely cultured in McCoy's 5a Modified Medium (ATCC), supplemented with 10% fetal bovine serum heat (ATCC) and 100 U/ml penicillin+100 μg/ml streptomycin (Sigma-Aldrich). CHO K1 cells were cultured in F-12K medium (ATCC), supplemented with 10% fetal bovine serum (ATCC) and 100 U/ml penicillin+100 μg/ml streptomycin (Sigma-Aldrich). Cell cultures were maintained in an incubator at 37° C., in a 5% $CO_2$ atmosphere.

The following stocks of hypoxia inducers were prepared: 200 mM of $CoCl_2$ in water (1000×), 50 mM of DFO (desferrioxamine, 250×) in DMSO or 250 mM of DMOG (dimethyloxalylglycine, N-[Methoxyoxoacetyl]glycine methyl ester, 250×) in DMSO. Stock solutions of the inducers were aliquoted and stored at −20° C. CD-1 and the control compound CD-3 were synthesized as described in Examples 1 and 2. Stock solutions (10 μM in DMSO, 2000×) of the probe and the control substances were prepared, aliquoted and stored at −20° C. in the dark. HP-1 kit for hypoxia detection (Hypoxyprobe Inc, Burlington, Mass.) was employed to confirm hypoxia induction in the cells.

The day before the experiment, the cells were seeded on 4-well microscope slides (Cel-Line™ Brand, Portsmouth, N.H.) at a density 1×10⁴ cells/well (2×10⁴ cells/cm²). On the day of the experiment, the cells were pre-loaded with either the hypoxia probe or control (5 μM final concentration in cell culture medium), and a hypoxic state was induced in the cells by the treatment with the following hypoxia inducers for 3.5 h at 37° C. and 5% $CO_2$: 0.2 mM of $CoCl_2$, 0.2 mM of DFO or 1 mM of DMOG. Alternatively, hypoxia was induced by the incubation of the cells for 3.5 h at 37° C. in a Billup-Rothenberg chamber (Billup-Rothenberg, Inc., San Diego, Calif.) in an anoxic environment (95% $N_2$, 5% $CO_2$). Post-treatment, the slides were washed twice with PBS, coverslipped and visualized using an Olympus BX-51 fluorescence microscope (FITC filter set, 490ex/525em).

In parallel, the hypoxia cellular state was detected using the hypoxia detecting reagent pimonidazole (Varia et al., 1998; Young, 1977). Briefly, the cells on the slides were preloaded with 0.2 mM pimonidazole in culture medium, treated with hypoxia inducers as described above, washed twice with PBS, fixed in methanol for 10 min at −20° C., re-hydrated in PBS, then blocked overnight at 4° C. using 3% BSA in PBS. Slides were stained with a 1:100 dilution of FITC-MAb1 against pimonidazole (HP-1 kit from Hypoxyprobe) for 45 min at 4° C., washed twice with PBS, coverslipped and visualized using an Olympus BX-51 fluorescence microscope equipped with an FITC filter set (490ex/525em). Cells not treated, not loaded with pimonidazole and not stained with FITC-MAb1 were used as negative controls.

The results of staining hypoxic HeLa cells are presented in FIG. 3. CD-1 was reduced by the nitroreductase enzyme present in hypoxic cells (both post-chemical induction of hypoxia, FIG. 3A, and anoxic treatment, left half of FIG. 3C) and the resulting reduction product spontaneously decomposed yielding a bright fluorescence signal. The control, CD-3, that cannot be reduced by nitroreductase did not yield any fluorescent signal (FIG. 3B and right half of FIG. 3C). The fluorescence pattern observed in hypoxic cells stained with CD-1 correlated with the pattern obtained after staining the cells with pimonidazole and fluorescently labeled monoclonal antibody (FIG. 3D). Staining of U-2 OS and CHO K1 cells treated with cobalt chloride, DFO or DMOG or subjected to anoxia demonstrated similar results (data not shown).

Example 8

Validation of Multi-Color Hypoxia Markers CD-1, CD-4, CD-5 and CD-6 Using Fluorescent Microscopy HeLa and U-2 OS cells were cultured as described in Example 7. Compounds CD-1, CD-4, CD-5 and CD-6 were dissolved in anhydrous DMSO at 10 mM concentration (1000× stock solutions). Stock solutions of the dyes were aliquoted and stored at −20° C. in the dark. All hypoxia inducer stocks were prepared as described in Example 7.

The day before the experiment, the cells were seeded on 4-well microscope slides (Cel-Line™ Brand, Portsmouth, N.H.) at a density 1×10⁴ cells/well (2×10⁴ cells/cm²). On the day of the experiment, the cells were preloaded with the hypoxia probes (5 μM final concentration for CD-1 and CD-5 probes, 1 μM final concentration for CD-4 and CD-6 probes in cell culture medium), and hypoxia was induced in the cells by the treatment with the following hypoxia inducers for 3.5 h at 37° C. and 5% $CO_2$: 0.2 mM of $CoCl_2$, 0.2 mM of DFO or 1 mM of DMOG. Alternatively, hypoxia was induced by the incubation of the cells for 3.5 h at 37° C. in a Billup-Rothenberg chamber (Billup-Rothenberg, Inc.) in an anoxic environment (95% of $N_2$, 5% of $CO_2$). Post-treatment, the slides were washed twice with PBS, coverslipped and visualized using an Olympus BX-51 fluorescence microscope with a DAPI filter set (350 ex/470em) for CD-5, an FITC filter set (490ex/525em) for CD-1, an orange filter set (550ex/620em) for CD-4 and a Texas Red filter set (596ex/670em) for CD-6.

Each tested self-immolative probe got efficiently processed in hypoxic HeLa cells yielding bright fluorescence signal in the corresponding area of spectrum (FIG. 4). Untreated cells did not show any fluorescence.

Example 9

Detection of Hypoxia with CD-1, CD-4 and CD-6 Using Flow Cytometry

HeLa and U-2 OS cells were cultured as described in Example 7. Human Jurkat T-cell leukemia cells (the A3 subclone) was obtained from ATCC and routinely cultured in RPMI-1640 medium (ATCC) supplemented with 10% fetal bovine serum (ATCC) and 100 U/ml penicillin+100 μg/ml streptomycin (Sigma-Aldrich). Cell cultures were maintained in an incubator at 37° C., with 5% $CO_2$ atmosphere. CD-1, CD-4 and CD-6 self-immolative hypoxia probes were prepared as described in Example 8. All hypoxia inducers stocks were prepared as described in Example 7.

The day before the experiment, HeLa and U-2 OS cells were seeded in 6-well tissue culture plates at a density $5\times10^5$ cells/well. Jurkat cells were collected in logarithmic phase of growth and aliquoted at a density $5\times10^5$ cells/sample. On the day of the experiment, the cells were preloaded with the hypoxia probes (5 μM final concentration for CD-1, 1 μM final concentration for CD-4 and CD-6 in cell culture medium), and the hypoxic state was induced in the cells as described in the Example 7. Post-treatment, the adherent cells (HeLa and U-2 OS) were collected by trypsinization, resuspended in 0.5 mL of fresh PBS and analyzed using flow cytometry. Jurkat cells were analyzed without washing.

Figure 5:
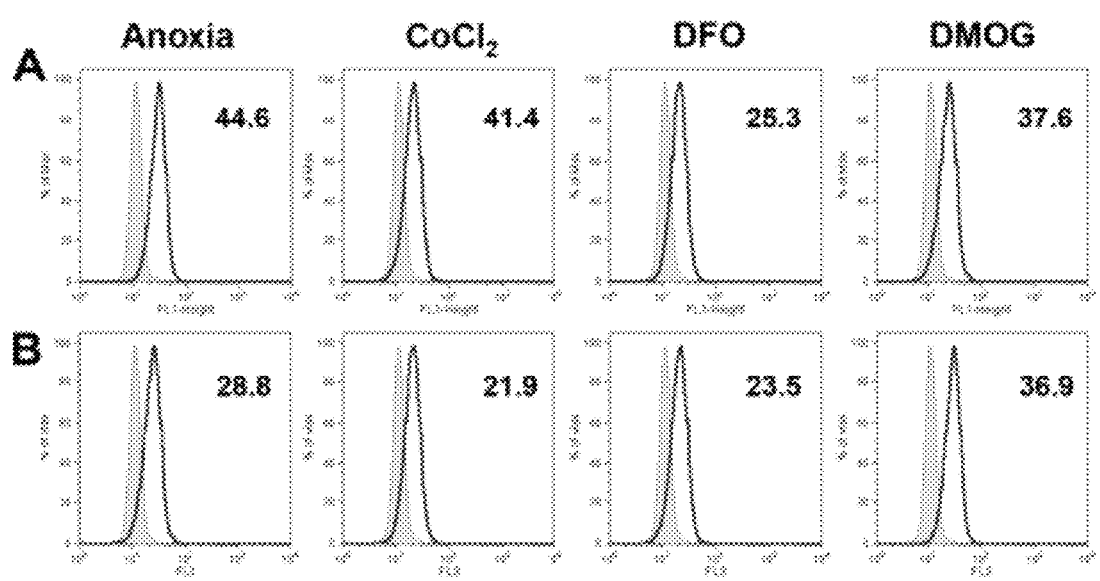
FIG. 5 is histograms showing hypoxia detection in Jurkat cells using flow cytometry and CD-1 (Panel A) and CD-6 (Panel B) hypoxia probes.
Figure 6A:
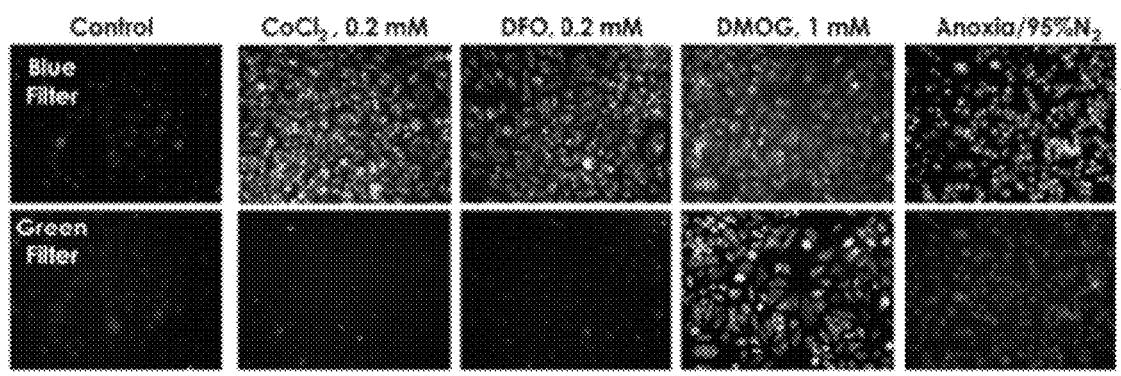
FIG. 6A-6C is micrographs showing multiplex detection of both cellular oxygen content and cellular redox status using hypoxia self-immolative probes and common ROS detecting reagents.
Figure 6A:
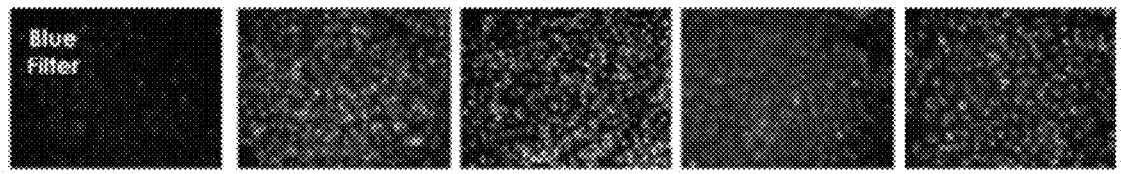
Figure 6A:
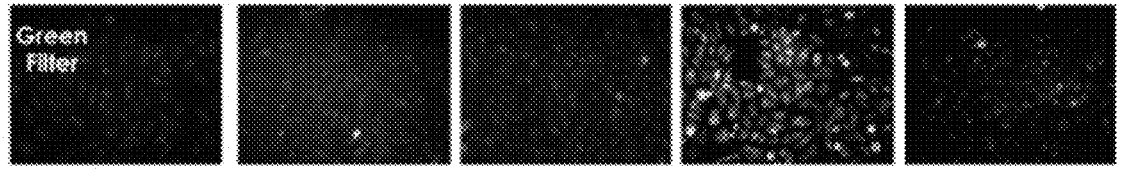
Figure 6B:
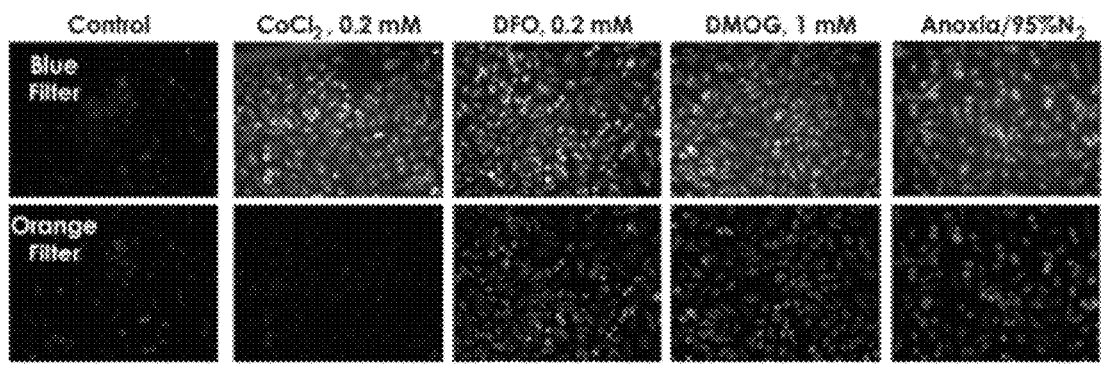
Figure 6B:
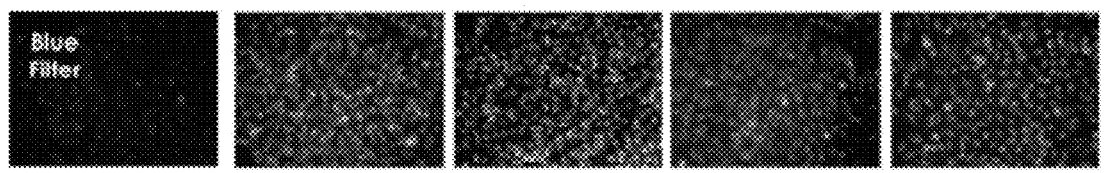
Figure 6B:
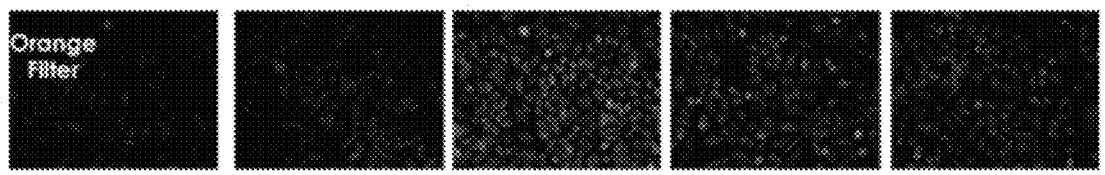
Figure 6C:
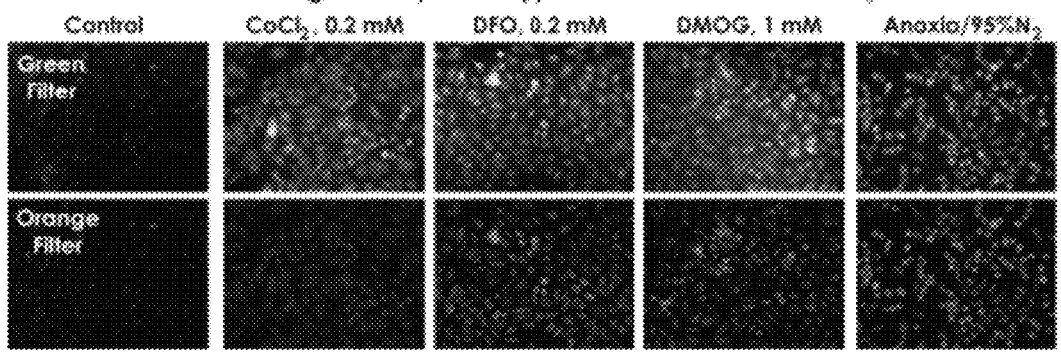
Figure 6C:
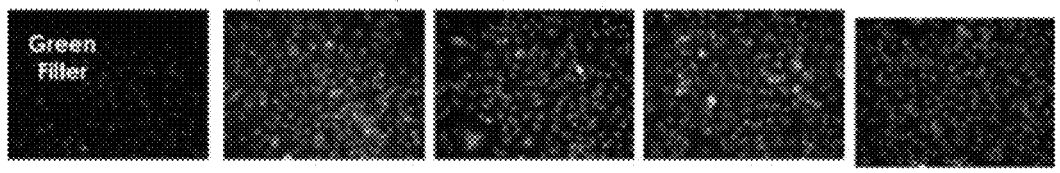
Figure 6C:
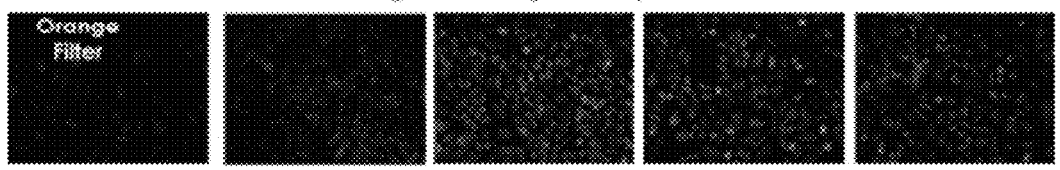

Flow cytometry experiments were performed using a FACS Calibur benchtop flow cytometer (BD Biosciences) equipped with a blue (488 nm) laser, and the fluorescence was recorded in the FITC (530/30 filter), PE (585/42 filter) and PerCP (670 LP filter) channels. Hypoxic cells were detected by detecting increases in fluorescence. The degree of hypoxia ($K_{hyp}$) can be quantified by using Kolmogorov-Smirnov statistics (Young, 1977) or the following formula:

$$K_{hyp}=(MFI_{hyp}-MFI_{con})/MFI_{hyp},$$

where $MFI_{hyp}$ and $MFI_{con}$ are median fluorescent intensities of hypoxia-induced and control cells, respectively. Alternatively, quantification can be approached by using quadrant and/or regions statistics that are usually embedded in flow cytometry software. The data, shown in FIG. 5, demonstrates a fluorescence increase in Jurkat cells loaded with probes CD-1 (panel A) or CD-6 (panel B) and treated with chemical hypoxia inducers ($CoCl_2$, DFO, DMOG) or subjected to anoxia. Cells loaded with the corresponding probes and treated with vehicle only are considered to be controls. The numbers on the histograms indicated the degree of hypoxia determined using the formula above (the values over 20 indicate hypoxic cellular state). Similar results were obtained for HeLa and U-2 OS cells (data not shown).

Example 10

Combined Detection of Hypoxia and Redox Status in Live Cells by Fluorescent Microscopy Using CD-1 and CD-5 Hypoxia Probes and Reactive Oxygen Species Detection Reagents HeLa and U-2 OS cells were cultured as described in Example 7. Stock solutions of CD-1 and CD-5 and various hypoxia inducers were prepared and stored as described in Examples 7 and 8. Additionally, 5 mM stock solutions (5000×) of 2',7'-dichloro-fluorescein diacetate (DCFDA, an indicator of global ROS generation) and dihydroethidium (DHE, specific indicator of superoxide generation) were made in anhydrous DMF. DMSO was avoided, since this solvent is a hydroxyl radical scavenger and its presence may affect ROS/RNS production in cellular systems. The following stocks of ROS inducers were prepared in DMF: 10 mM pyocyanin (general ROS generating compound, 100×), 20 mM antimycin A (general ROS inducer, 400×), 50 mM pyrogallol (a superoxide radical generator, 1000×), 1 mM t-butyl hydroperoxide (TBHP, peroxide radical inducer, 10,000×). ROS probes and inducers were aliquoted and stored at −80° C.

The day before the experiment, the cells were seeded on 4-well microscope slides (Cel-Line™ Brand, Portsmouth, N.H.) at a density $1\times10^4$ cells/well ($2\times10^4$ cells/cm$^2$). On the day of the experiment, the cells were preloaded with both hypoxia probe (5 μM final concentration in cell culture medium) and ROS detecting reagent with suitable spectral characteristics. Two ROS-detecting probes, DCFDA and DHE, were used in a pilot experiment in conjunction with hypoxia self-immolative probes. The hydrolyzed product of DCFDA, DCFH, is considered to be a general indicator of ROS, reacting with $H_2O_2$ (in the presence of peroxidases), $ONOO^-$, lipid hydroperoxides, and hydroxyl radicals. The oxidized product can be detected by strong fluorescence emission at around 525 nm when excited at around 488 nm. Because $H_2O_2$ is a secondary product of $O_2.^-$, DCFH fluorescence has been used to implicate $O_2.^-$ production. The direct reaction of DHE with $O_2.^-$ yields a very specific fluorescent product, requiring no conversion to $H_2O_2$. The product of the DHE reaction with $O_2.^-$ fluoresces strongly at around 600 nm when excited at 500-530 nm.

Tested pairs of the probes were as follows: CD-5 with DCFDA or DHE, and CD-1 with DHE. A hypoxic state was induced in the cells as described in Example 7. Control slides were singly-stained with hypoxia or ROS-detecting probes only. Additional slides were treated with different general and specific ROS inducers and stained with ROS-detecting probes to control ROS staining. Post-treatment, the slides were washed twice with PBS, coverslipped and visualized using an Olympus BX-51 fluorescence microscope and a DAPI filter set (350 ex/470em) for CD-5, an FITC filter set (490ex/525em) for CD-1 or for total ROS detection reagent, and an orange filter set (550ex/620em) for HE.

The results of this experiment are presented in FIG. 6. While CD-1 and CD-5 probes generated bright fluorescent signal in all four hypoxic samples of HeLa cells (anoxia-exposed or treated with $CoCl_2$, DFO and DMOG), ROS-detecting dyes give more individually distinct results. Abundant superoxide production was detected in anoxic DFO and DMOG-treated cells, while in $CoCl_2$-treated samples there was only moderate staining with the superoxide detection reagent. At the same time, peroxides/peroxynitrite formation was detected in DMOG-treated cells only. Comparison of the result of the double staining with hypoxia and ROS detecting probes with the results of separate staining with either probe validated obtained results and demonstrated that above-mentioned probes are compatible for multiplexed detection of both hypoxia and/or redox status of the cell.

Example 11

Combined Detection of Hypoxia and Superoxide in Live Cells by Flow Cytometry Using CD-1 and CD-6 Hypoxia Probes and Superoxide Detection Reagent HeLa, U-2 OS, and Jurkat cell lines were cultured as described in Examples 7 and 9. Stock solutions of the probes and inhibitors were prepared as described in Examples 7 and 10.

The day before the experiment, HeLa and U-2 OS cells were seeded in 6-well tissue culture plates at a density of $5 \times 10^5$ cells/well. Jurkat cells were collected in logarithmic phase of growth and aliquoted at a density of $5 \times 10^5$ cells/sample. On the day of the experiment, the cells were preloaded with either hypoxia or ROS-detecting probes only or with the combination of hypoxia and ROS-detecting probes with compatible spectral characteristics. Samples stained with single hypoxia probes or with two ROS-detecting probes were made to validate data obtained with the combination of hypoxia and redox probes. The probes used in the experiment and their final concentrations in cell culture medium were as follows: CD-1 (5 μM) and CD-6 (1 μM), DCFDA, peroxide/peroxynitrite/hydroxyl detection probe and HE, specific superoxide detection reagent (1 μM for both redox probes). Hypoxia was induced in the cells as described in Example 7. Additionally, cells were treated with different general and specific ROS inducers and stained with ROS-detecting probes to control ROS production and staining. Post-treatment, the adherent cells (HeLa and U-2 OS) were collected by trypsinization, re-suspended in 0.5 mL of fresh PBS and analyzed using flow cytometry. Jurkat cells were analyzed without washing. Flow cytometry experiments were performed using an FACS Calibur benchtop flow cytometer (BD Biosciences) equipped with a blue (488 nm) laser, and the fluorescence was recorded in the FITC (530/30 filter), PE (585/42 filter) and PerCP (670 LP filter) channels. Data were collected uncompensated, also compensation corrections were performed using unstained cells, and cells stained with each single dye separately (CD-1, CD-6, DCFDA or HE). To quantify data, quadrant gates were set using untreated samples.

Figure 7A:
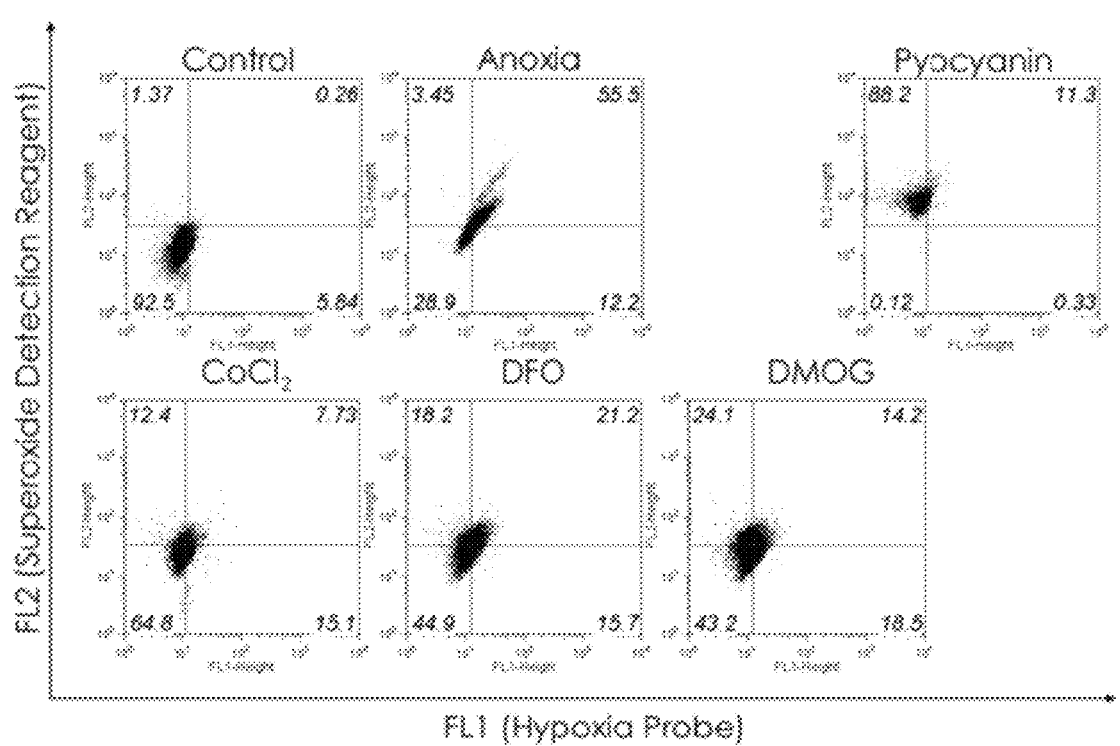
FIG. 7A-7C show histograms depicting results of multiplex flow cytometry assays for combined detection of hypoxia and redox status in live cells. The numbers in the quadrants of the dot plots indicate percentage of the cells.
Figure 7B:
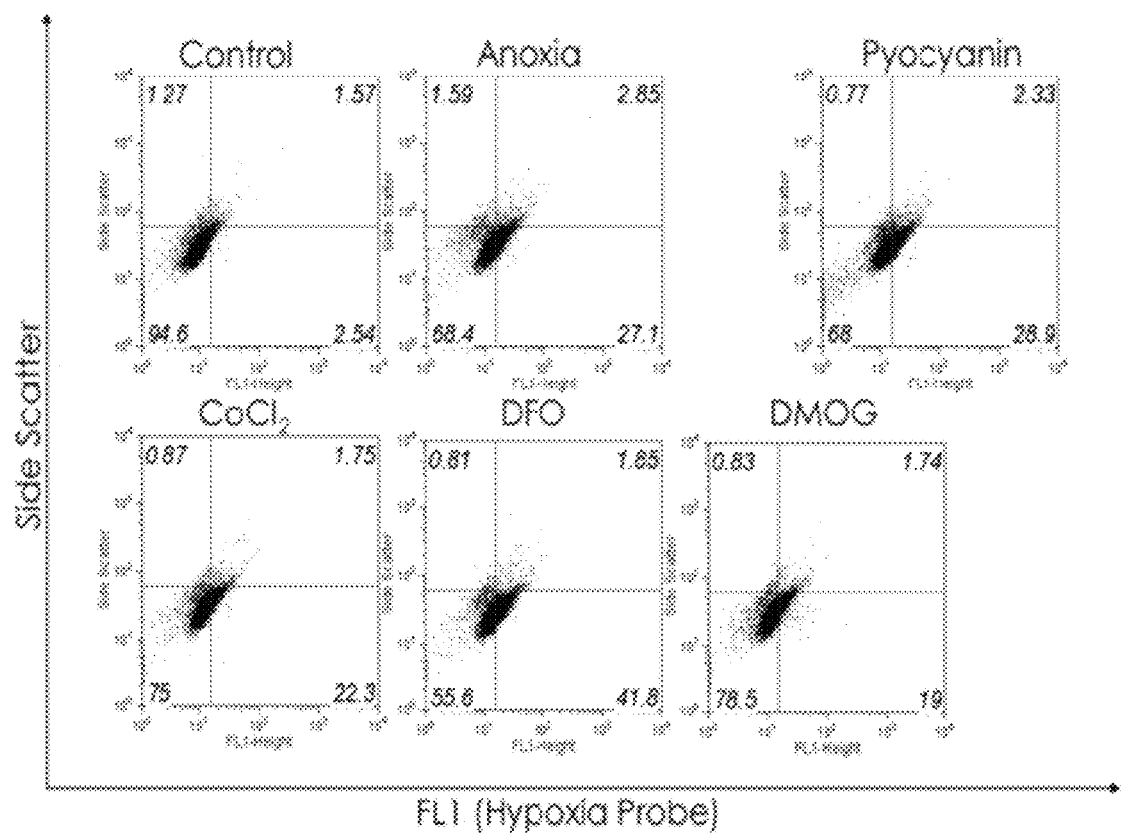
Figure 7C:
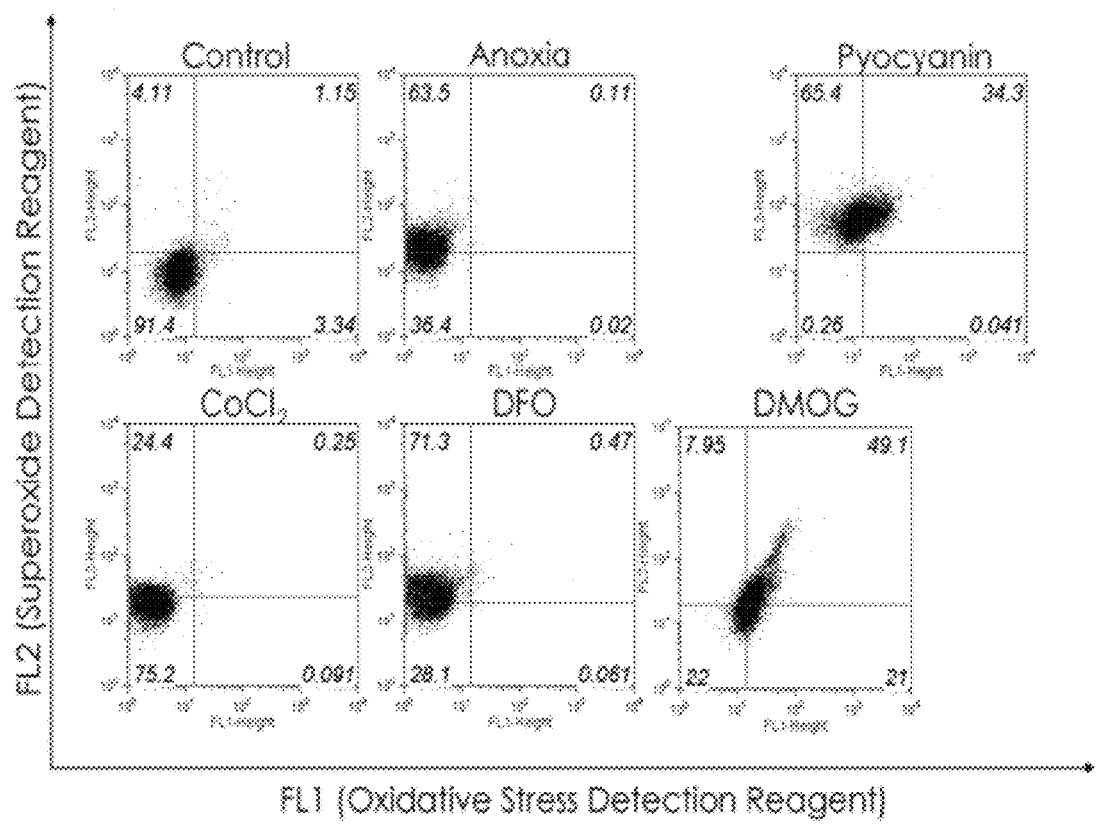
Figure 8A:
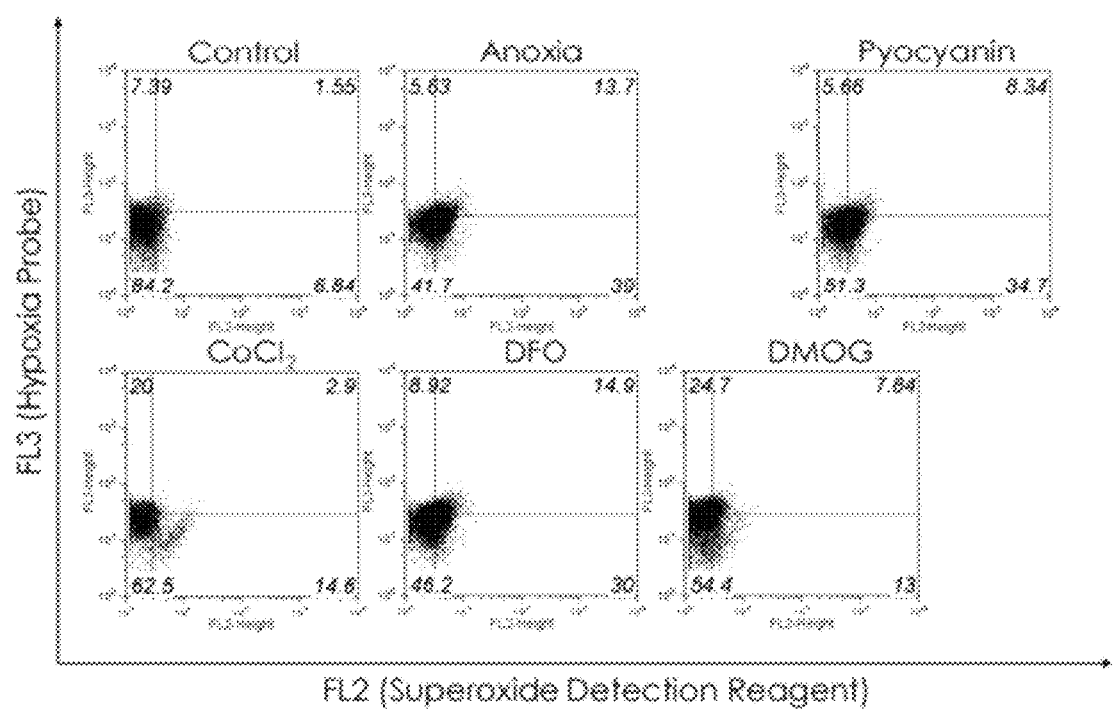
FIG. 8A-8D show histograms depecting results of multiplex flow cytometry assays for combined detection of hypoxia and redox status in live cells. The numbers in the quadrants of the dot plots indicate percentage of the cells.
Figure 8B:
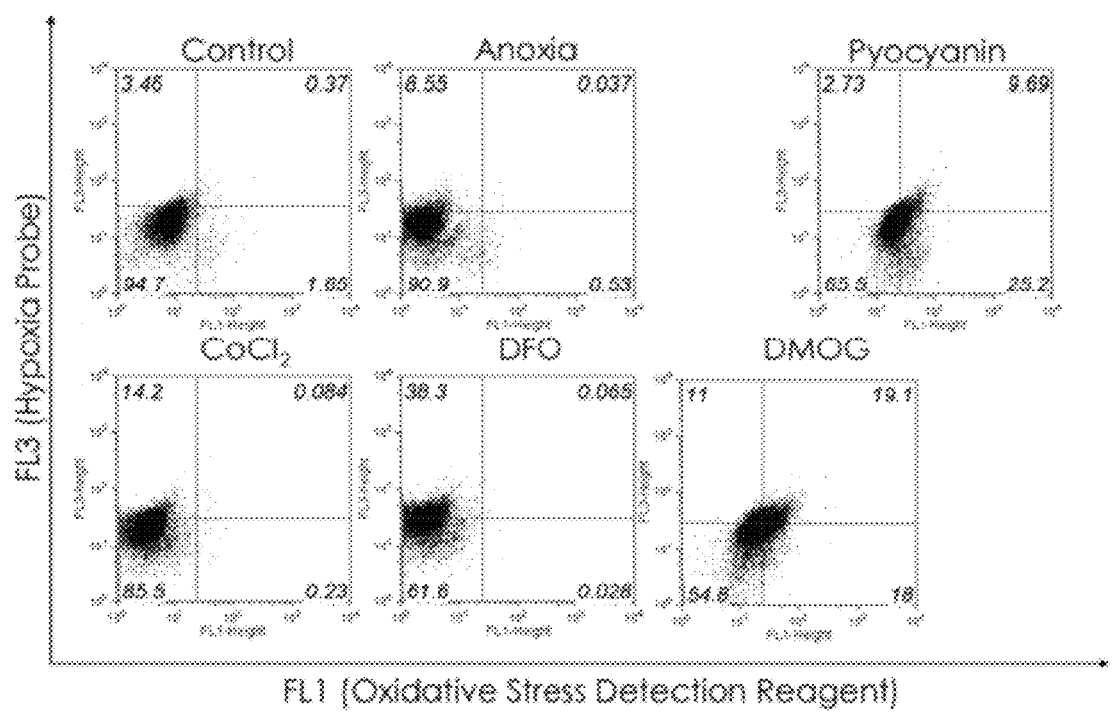
Figure 8C:
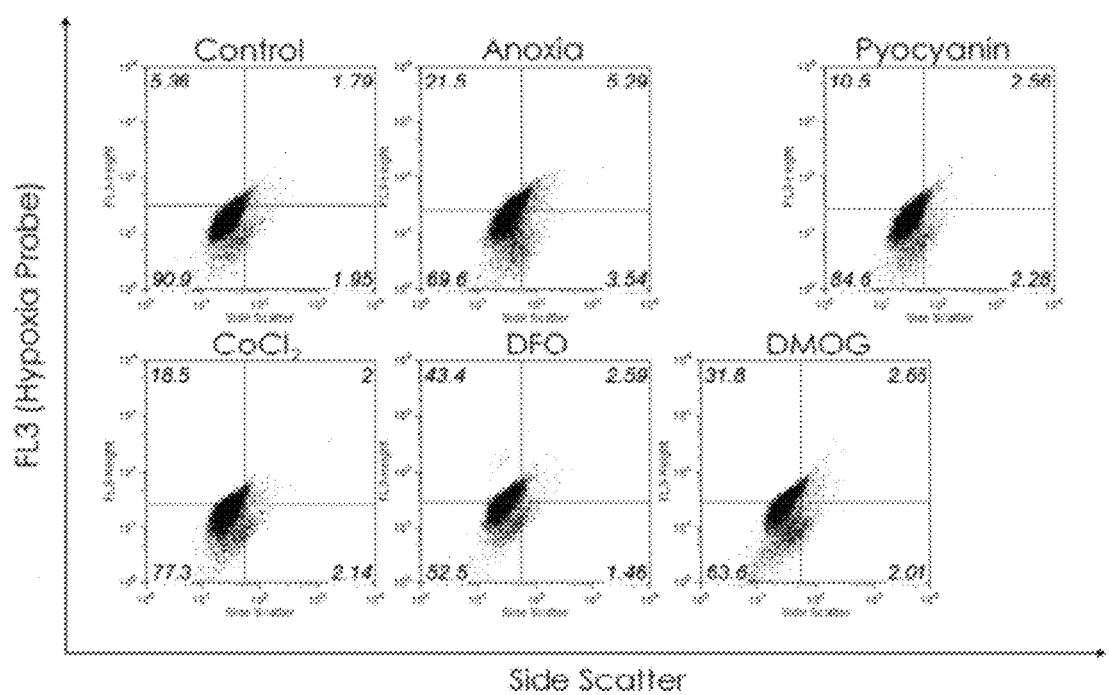
Figure 8D:
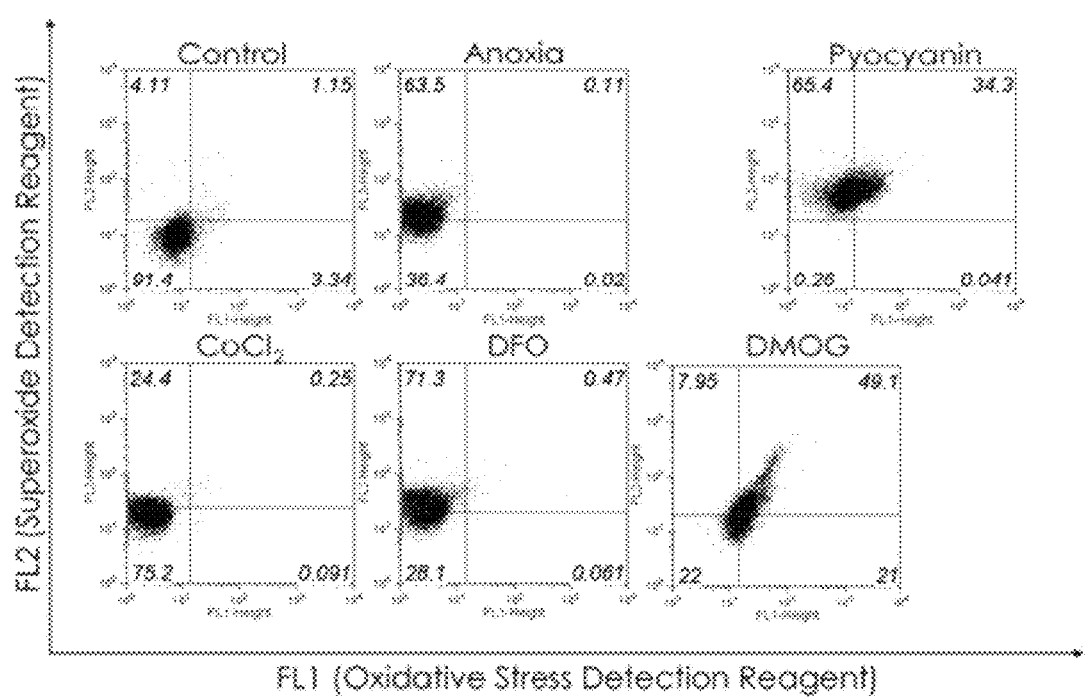

The results of pilot experiments are presented in FIGS. 7 and 8. When CD-1 was used in combination with the superoxide detection reagent in Jurkat cells treated as described earlier, the increased population of green positive cells was detected by flow cytometry in each hypoxia-induced sample (FIG. 7, panel A). Simultaneously, significant superoxide production was detected in anoxic, DFO- and DMOG-treated samples by increased population (40% and more compared to the untreated cells) of orange positive cells. In $CoCl_2$-treated samples, superoxide production was moderate—about 20% of orange positive cells. Pyocyanin-treated cells (positive control for ROS production) display high superoxide production (as expected) and a moderate hypoxia state (about 10% of the positive green cells). Cells stained with the CD-1 probe only exhibit similar numbers for green positive populations (FIG. 7, panel B). Staining with ROS-detecting reagents also corroborated superoxide production data for hypoxia-induced Jurkat cells (FIG. 7, panel C).

Similar results were obtained for the combination of CD-6 with DCFDA or with HE dyes (FIG. 8). The hypoxia probe was able to detect hypoxic cell populations when employed in combination with any of ROS detecting dyes (FIG. 8, panels A and B) or alone (Panel C). The data was corroborated by staining of pyocyanin-treated cells (positive control for ROS production) and also by analyzing samples stained with ROS-detecting dyes (panel D).

Example 12

Detection of Hypoxia in Live Cells Using Hypoxia Probes and Multiplate Fluorescence Reader HeLa, U-2 OS, and Jurkat cell lines were cultured as described in Examples 7 and 9. Stock solutions of the probes and inducers were prepared as described in Examples 7 and 8. Two protocols (using cells in suspension and using adherent cells) were used.

A. For the first protocol (suspension cells), cells in suspension ($5 \times 10^5$ cells/100 μL) were added to the wells of 96-well black walled microplates where medium containing hypoxia probes (5 μM final concentration for CD-1 and CD-5, 1 μM for CD-4 and CD-6) and chemical hypoxia inducers ($CoCl_2$, DFO or DMOG) or vehicle were added. Additionally hypoxia was induced by incubation of the cells in anoxic environment (Billup-Rothenberg chamber, 5% $CO_2$, 95% $N_2$) as described in Example 6. Cells were incubated for 3.5 hrs at 37° C. Fluorescence was then immediately measured by fluorescence microplate reader. Alternatively, after the incubation, plates were centrifuged (5 min, 200×g), the supernatant was removed, the cells were resuspended in 200 μL of cold tissue culture medium and retained fluorescence was measured. In some cases, cells were washed with cold PBS after staining.

B. For adherent cells, the cells were seeded in black walled 96-well microplates (0.5–2.0×$10^5$ cells/well). Twenty four hrs later, medium containing hypoxia probes (5 μM final concentration for CD-1 and CD-5, 1 μM for CD-4 and CD-6) and chemical hypoxia inducers ($CoCl_2$, DFO or DMOG) or vehicle were added to the cells for 3.5 hrs at 37° C. Additionally hypoxia was induced by incubation of the cells in an anoxic environment (Billup-Rothenberg chamber, 5% $CO_2$, 95% $N_2$). Fluorescence was then measured by fluorescence microplate reader immediately or after excess dye(s) was removed by washing with PBS.

The probe(s) fluorescence was measured using an OPTIMA FluoStar multiplate fluorimeter (BMG Labtech Inc., NC) equipped with 340, 490 and 550 nm excitation filter and 480, 520, 570 and 610 nm emission filters, or Synergy™ Mx BioTek multi-mode microplate reader (BioTek Instruments Inc., VT) using 378, 490 and 520 nm excitation and 488, 520, 540 and 600 nm emission settings. The results of the assay were normalized to the fluorescence of the empty well and expressed as a ratio of the fluorescence of the inducer-treated cells to the fluorescence of the untreated control cells.

Figure 9:
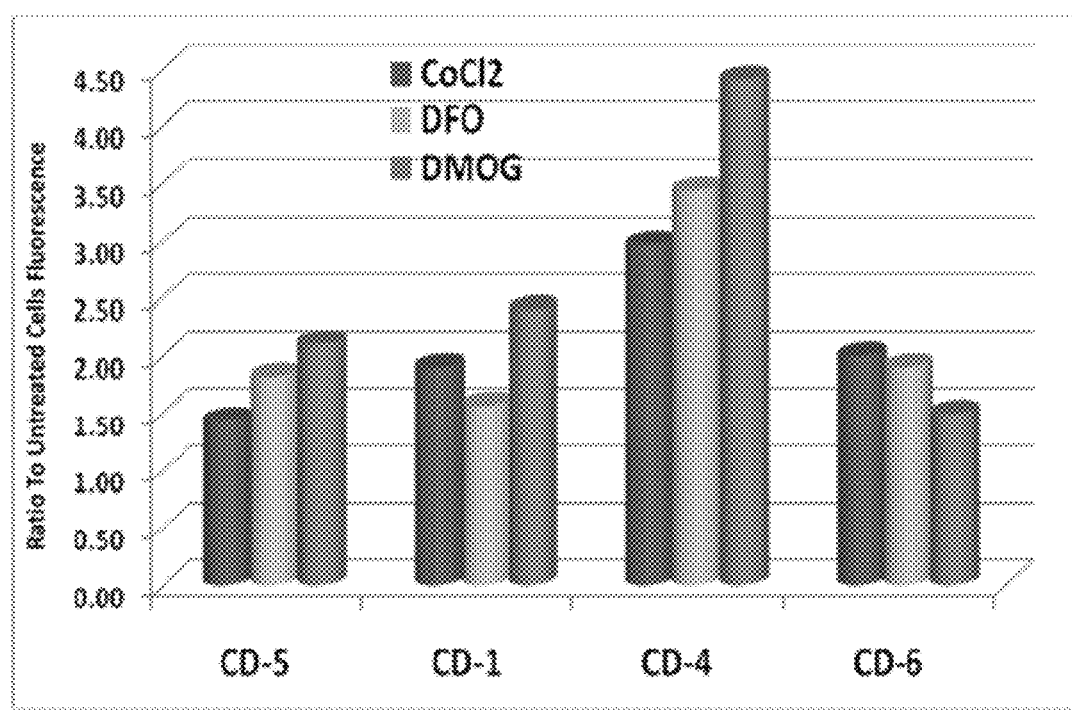
FIG. 9 is a bar graph showing ratios of fluorescence generated in hypoxia-induced HeLa cells to fluorescence of untreated cells.

Results of hypoxia detection using a fluorescence microplate reader are presented in FIG. 9 and are similar to the results obtained by fluorescence microscopy and flow cytometry methods.

Example 13

Synthesis of CD-8 a). Preparation of CD-9

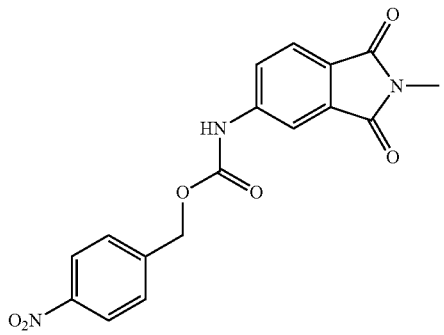

CD-9

To 100 mg of 4-amino-N-methylphthalimide in 3 ml of dimethylformamide, 0.5 ml of pyridine was added followed by 300 mg of p-nitrobenzyl chloroformate. The reaction mixture was allowed to stir overnight and the solvent was removed in vacuo. The residue was dissolved in chloroform and purified on Biotage SP4 System with SNAP 25 g column and chloroform methanol gradient to give off-white product (110 mg).

b). Preparation of CD-8

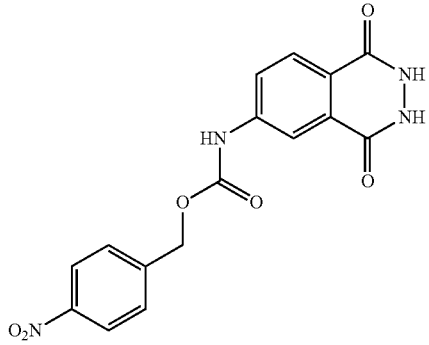

CD-8

To 20 mg of CD-9 in 3 ml of methanol, 0.5 ml of hydrazine was added. The reaction mixture was stirred for 1 hour at room temperature and the solvent was removed in vacuo. The residue was dissolved in chloroform and purified on Biotage SP4 System with SNAP 25 g column and chloroform methanol gradient to give off-white product (15 mg).

Example 14

Chemical Reduction of CD-8 and Enzymatic Testing of the Reduction Product

Figure 10:
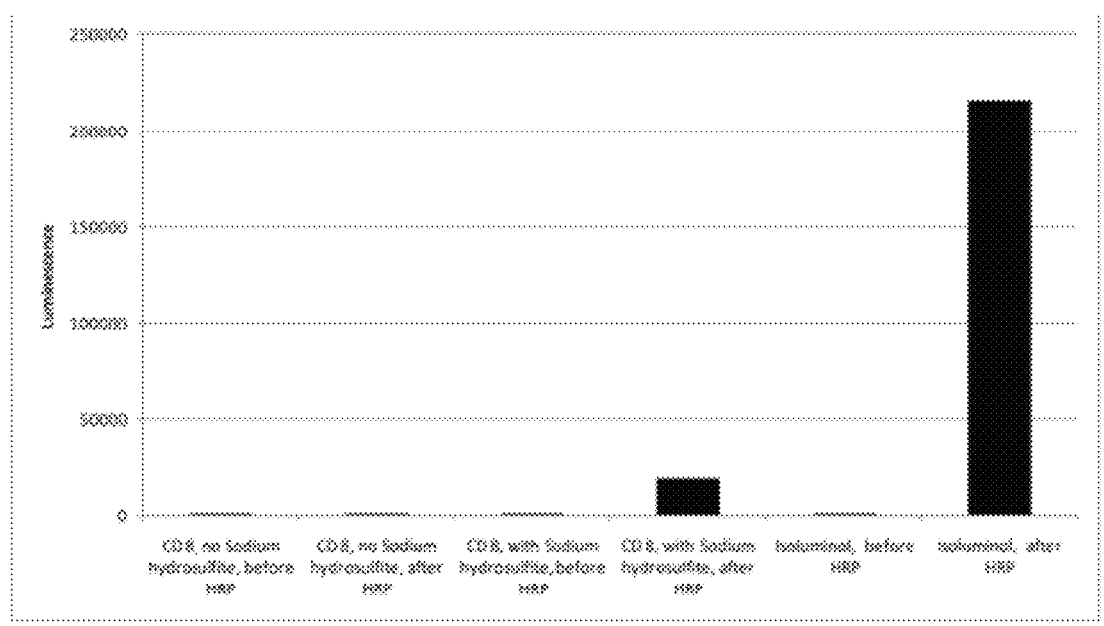
FIG. 10 is a bar graph showing luminance of compound CD-8 after various treatments.

100 μl of 200 μM CD-8 (dissolved in 1×PBS buffer) with (1 mM) or without sodium hydrosulfite was incubated in a 96 black microplate (Greiner®) at room temperature for 1 hour. Also included was a positive control of 100 μl of 50 μM of isoluminol dissolved in 1×PBS buffer. A 4:1 volumetric mixture (1.25 μL) of stabilized $H_2O_2$ (Roche Diagnotics GmbH: Reference number: 11 582 950 001, component 2) and 200 mM of 4-idophenol was then added. Before adding horseradish peroxidase (HRP), the background luminescence was recorded; after adding 2 μL of 50 μM HRP, the luminescence was immediately recorded on a Biotek® plate reader. The results are summarized in FIG. 10. Sodium hydrosulfite clearly triggered the reduction of the nitro group of CD-8 into an amino group, triggering the self-immolative release of isoluminol.

REFERENCES

Anastasio and Matthew, Atmos. Chem. Phys., 2006. 6:2439-2451.
Chandran, S. S., Dickson, K. A., Raines, R. T., Latent Fluorophore Based on the Trimethyl Lock. J. Am. Chem. Soc., 2005. 127:1652-1653.
Danieli, E. and Shabat, D., Bioorganic & Medicinal Chem., 2007. 15:7318-7324.
Duimstra, J. A. et al., J. Am. Chem. Soc., 2005. 127:12847-12855.
Gao, W. et al., J. Am. Chem. Soc., 2003. 125:11146-11147.
Ho, N-H. et al., Bioorganic & Medicinal Chem. Lett., 2006. 16:2599-2602.
Huang, Sheng-Tung and Yuh-Ling Lin; Org. Lett., 2006. 8:265-268.
Huang, Sheng-Tung et al., Analytical Chemistry, 2010. 82:7329-7334.
Jones, G. B., et al., Bioorganic & Medicinal Chemistry, 2006. 14:418-425.
Matthew and Anastasio, Atmos. Chem. Phys., 2006. 6:2423-2437.
Meyer, Y. et al., Org. Lett., 2008. 10:1517-1520.
Nagano, J. Clin. Biochem. Nutr., 2009. 45:111-124.
Nakata, E., et al., Bioorg. Med. Chem., 2009. 17:6952-6958.
Nunn, A., K. Linder, and H. W. Strauss, Nitroimidazoles and imaging hypoxia. Eur J Nucl Med, 1995. 22:265-80.
Ojima, Accounts Of Chemical Research, 2008. 41:108-119.
Pires, M. M. and Jean Chmielewski, Org. Lett., 2008. 10:837-840.
Richard et al., Org. Lett., 2007. 9:4853-4855.
Richard et al., Bioconjugate Chem., 2008a. 19:1707-1718.
Richard et al., Org. Lett., 2008b. 10:4175-4178.
Sagi, A. et al., J. Am. Chem. Soc., 2008. 130:5434-5435
Tarpey et al., A. J. Physiol. Regul. Integr. Comp. Physiol., 2004. 286:R431-R444.
Ueno et al., J. Am. Chem. Soc. 2006. 128:10640-10641.
Varia, M. A., et al., Pimonidazole: a novel hypoxia marker for complementary study of tumor hypoxia and cell proliferation in cervical carcinoma. Gynecol Oncol, 1998. 71:270-7.
Yatzeck, M. M. et al., Bioorganic & Medicinal Chemistry Letters, 2008. 18:5864-5866.
Young, I. T., Proof without prejudice: use of the Kolmogorov-Smirnov test for the analysis of histograms from flow systems and other sources. J Histochem Cytochem, 1977. 25:935-41.
PCT Patent Publication WO2008/030120.
U.S. Pat. No. 7,445,891.
U.S. Pat. No. 7,534,902.
U.S. Pat. No. 7,569,695.
U.S. Pat. No. 7,579,140.
U.S. Pat. No. 7,737,281.
U.S. Pat. No. 7,754,681.
U.S. Pat. No. 7,662,973.
US Patent Publication US2002/0031795.
US Patent Publication US2003/0186348.
US Patent Publication US2005/0271615.

US Patent Publication US2009/0253118
US Patent Publication US2009/0336954.
US Patent Publication US2010/0068752.
US Patent Publication US2010/0062460.
US Patent Publication US2010/0081159.
US Patent Publication US2010/0093004.
US Patent Publication US2010/0173332.
U.S. patent application Ser. No. 12/799,853, filed May 3, 2010.

In view of the above, it will be seen that several objectives of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A compound selected from:

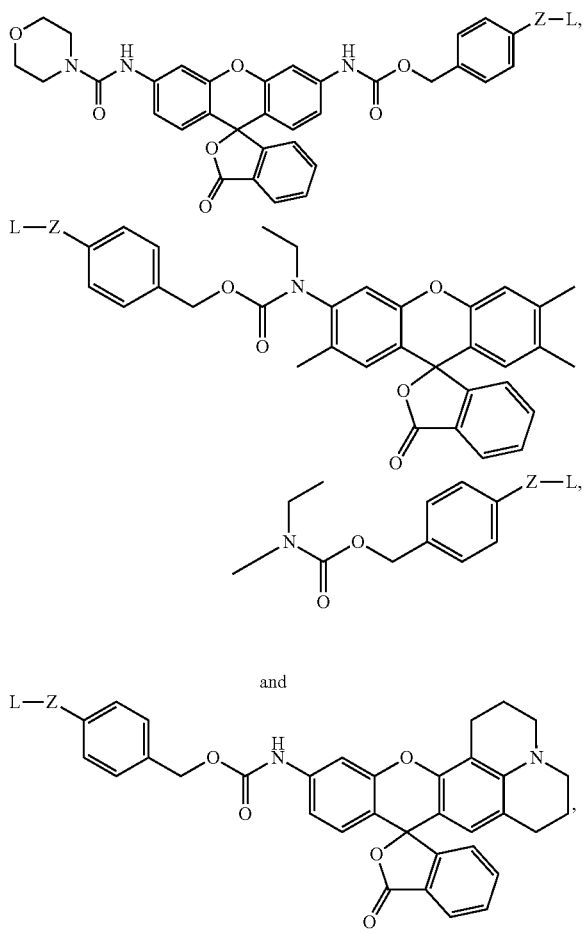

and wherein Z is a reducible nitrogen-containing group selected from the group consisting of a nitro group ($NO_2$), an azo group (—N=N), a hydrazo group (NH—NH), a nitroso group (NO), and a hydroxylamino group (NHOH), or an amino group with an electron-deficient moiety, or Z is amino group with an electron-deficient moiety selected from the group consisting of carbonyl (C=O), phosphoryl ($PO_3^{2-}$) and sulfonyl ($SO_3^-$); and wherein L is nothing when Z is a reducible nitrogen-containing group, or L is an unsubstituted straight-chain, branched or cyclic alkyl, alkenyl or alkynyl group, a substituted straight-chain, branched or cyclic alkyl, alkenyl or alkynyl group wherein one or more C, CH or $CH_2$ groups are substituted by an O atom, N atom, S atom, or NH group, an unsubstituted or substituted aromatic group, or a linear or branched sequence of amino acids.

2. A compound of claim 1 wherein L is nothing and Z is $NO_2$.

3. A method of determining whether a cell comprises a nitroreductase, the method comprising
    (a) incubating the cell with a compound of claim 2 for a time and under conditions sufficient for the compound to enter the cell and be exposed to a nitroreductase if present in the cell; and
    (b) determining if a signal greater than the signal generated by the compound when not exposed to a nitroreductase is generated,
    wherein a greater signal indicates that the cell comprises the nitroreductase.

4. A method of determining whether a mammalian cell is hypoxic, the method comprising
    (a) incubating the cell with a compound of claim 2 for a time and under conditions sufficient for the compound to enter the cell and be exposed to a nitroreductase if present in the cell, wherein the nitroreductase is indicative or hypoxia in the cell; and
    (b) determining if a signal greater than the signal generated by the compound when not exposed to a nitroreductase is generated,
    wherein a greater signal indicates that the cell is hypoxic.

5. A method of detecting a microorganism that comprises a nitroreductase, the method comprising
    (a) incubating the microorganism with a compound of claim 2 for a time and under conditions sufficient for the compound to enter the cell and be exposed to a nitroreductase if present in the microorganism; and
    (b) determining if a signal greater than the signal generated by the compound when not exposed to a nitroreductase is generated,
    wherein a greater signal indicates that the microorganism comprises a nitroreductase.

6. A method of identifying nitroreductase in a sample, the method comprising
    (a) incubating the sample a the compound of claim 2, and
    (b) determining if a signal greater than the signal generated by the compound when not exposed to a nitroreductase is generated,
    wherein a greater signal indicates that the sample comprises a nitroreductase.

7. A method of detecting hydrosulfite in a sample, the method comprising
    (a) combining the sample with a compound of claim 2, then
    (b) determining if a signal greater than the signal generated by the compound when not exposed to a nitroreductase is generated,
    wherein a greater signal indicates that the sample comprises a hydrosulfite.

* * * * *